US005910488A

United States Patent [19]
Nabel et al.

[11] Patent Number: 5,910,488
[45] Date of Patent: Jun. 8, 1999

[54] PLASMIDS SUITABLE FOR GENE THERAPY

[75] Inventors: Gary J. Nabel; Elizabeth G. Nabel, both of Ann Arbor, Mich.; Denise Lew, Encinitas; Magda Marquet, La Jolla, both of Calif.

[73] Assignee: Vical Incorporated, San Diego, Calif.

[21] Appl. No.: 08/564,313

[22] PCT Filed: May 27, 1994

[86] PCT No.: PCT/US94/06069

§ 371 Date: Dec. 1, 1995

§ 102(e) Date: Dec. 1, 1995

[87] PCT Pub. No.: WO94/29469

PCT Pub. Date: Dec. 22, 1994

Related U.S. Application Data

[63] Continuation-in-part of application No. 08/074,344, Jun. 7, 1993, abandoned.
[51] Int. Cl.$^6$ .......................... A61K 48/00; C12N 15/63; C12N 15/79; C12N 15/09
[52] U.S. Cl. .................. 514/44; 435/320.1; 435/172.3; 435/69.1; 435/375; 935/56; 935/71; 935/33
[58] Field of Search .......................... 514/44; 435/320.1, 435/172.3, 325, 375, 69.1; 536/23.1; 935/52, 54, 56, 71, 33

[56] References Cited

U.S. PATENT DOCUMENTS 5,580,859  12/1996  Felgner ..................................... 514/44

FOREIGN PATENT DOCUMENTS 930005  1/1993  WIPO .

OTHER PUBLICATIONS

Alexander, P. (1973) Activated macrophages and the antitumor action of BCG. Natl. Cancer Inst. Monogr. 39:127–133.
Barbosa, J. et al. (1982) Identification of human genomic clones coding the major histocompatibility antigens HLA–A2 and HLA–B7 by DNA–mediated gene transfer. Proc. Natl. Acad. Sci. 79:6327–6331.
Bjorkman, P.J. et al (1990) Structure, function, and diversity of class 1 major histocompatibility complex molecules. Annu. Rev. Biochem. 59:253–288.
Canonico, A., et al. (1991) Expression of a CMV promoter driven human α–1 antitrypsin gene in cultured lung endothelial cells and in the lungs of rabbits. Clinical Research 39(2):219A.
Carlow, D.A. et al. (1989) Failure of expression of class I major histocompatibility antigens to alter tumor immunogenicity of a spontaneous murine carcinoma. J. Natl. Canc. Inst. 81:759–767.
Chamberlain, J., et al. (1988) Tissue–specific and cell surface expression of human major histocompatibility complex class I heavy (HLA–B7) and light $β_2$–microglobulin) chain genes in transgenic mice. Proc. Natl. Acad. Sci. 85:7690–7694.

Chou, T. et al. (1988) Generation of therapeutic T lymphocytes from tumor–bearing mice by in vitro sensitization. Culture requirements and characterization of immunologic specificity. J. Immunol. 140:2453–2461.
Clark, S.C. et al. (1987) The human hematopoietic colony–stimulating factors. Science 236:1229–1237.
Cole, G.A. et al. (1987) Allogeneic H–2 antigen expression is insufficient for tumor rejection. Proc. Natl. Acad. Sci. USA 84:8613–8617.
Fearon, E.R. et al. (1990) Interleukin–2 production by tumor cells bypasses T helper function in the generation of an antitumor response. Cell 60:397–403.
Felgner, P.L. et al. (1987) Lipofection: A highly efficient, lipid–mediated DNA–transfection procedure. Proc. Natl. Acad. Sci. 84:7413–7417.
Felgner, P.L. et al. (1989) Cationic liposome–mediated transfection. Focus 11(2):21–25.
Funa, K. et al. (1986) Paucity of $β_2$–microglobulin expression on small cell lung cancer, bronchial carcinoids and certain other neuroendocrine tumors. Lab Invest. 55:186–193.
Gao, X. et al. (1991) A novel cationic liposome reagent for efficient transfection of mammalian cells. Biochem. Biophys. Res. Commun. 179:280–285.
Gopas, J. et al. (1989) The relationship between MHC antigen expression metastasis. Adv. Cancer Res. 53:89–115.
Gorman, C. et al. (1982) Recombinant genomes which express chloramphenicol acetyltransferase in mammalian cells. Mol. Cell. Biol. 2:1044–1051.
Gorman, C. et al. (1983) High efficiency DNA–mediated transformation of primate cells. Science 221:551–553.
Gussow, D., et al. (1987) The human $β_2$–microglobulin gene. Journal of Immunology 139:3132–3138.
Hammerling, G.J. et al. (1986) Manipulation of metastasis and tumour growth by transfection with histocompatibility class I genes. J. Immunogenet. 13:153–157.
Herberman, R.B. (1985) Multiple functions of natural killer cells, including immunoregulation as well as resistance to tumor growth. Concepts Immunopathol. 1:96–132.
Hersh, E., et al. (1994) Phase I study of immunotherapy of malignant melanoma by direct gene transfer. Human Gene Therapy 5:1371–1384.
Holden, C.A. et al. (1983) Absence of human leukocyte antigen molecules in skin tumors and some cutaneous appendages: Evidence using monoclonal antibodies. J. Am. Acad. Dermatol. 9:867–871.
Hosokawa, M. et al. (1983) Alteration of immunogenicity of xenogenized tumor cells in syngeneic rats by the immune responses to virus–associated antigens produced on immunizing cells. Cancer Res. 43:2301–2305.

(List continued on next page.)

*Primary Examiner*—Brian R. Stanton
*Assistant Examiner*—Karen M. Hauda
*Attorney, Agent, or Firm*—Knobbe, Martens, Olson & Bear, LLP

[57] ABSTRACT

The invention provides vectors adapted for use in transferring into tissue or cells of an organism genetic material encoding one or more cistrons capable of expressing one or more immunogenic or therapeutic peptides and related methods.

22 Claims, No Drawings

OTHER PUBLICATIONS

Hui, K. et al. (1984) Rejection of transplantable AKR leukaemia cells following MHC DNA–mediated cell transformation. Nature 311:750–752.

Invitrogen Molecular Biology Products, San Diego. 1991 Catalog. p. 28, plasmid pRc/RSV.

Isakov, N. et al. (1983) Loss of expression of transplantation antigens encoded by the h–2K locus on Lewis lung carcinoma cells and its relevance to the tumor's metastatic properties. J. Natl. Canc. Inst. 71:139–145.

Itaya, T. et al. (1987) Xenogenization of a mouse lung carcinoma (3LL) by transfection with an allogeneic class I major histocompatibility complex gene $(H-2L^d)^{1.}$ Cancer Res. 47:3136–3140.

Johnson, C.S. et al. (1990) Immunotherapeutic approaches to leukemia: The use of the friend virus–induced erythroleukemia model system. Cancer Res. 50:5682–5686.

Johnson, C.S. et al. (1989) Lymphokine–activated killer cell plus recombinant interleukin–2 therapy of erythroleukemia in mice. Leukemia 3:91–96.

Klein, G. et al. (1977) Immune surveillance against virus–induced tumors and nonrejectability of spontaneous tumors: Contrasting consequences of host versus tumor evolution. Proc. Natl. Acad. Sci. USA 74:2121–2125.

Kozak, M. (1987) An analysis of 5'–noncoding sequences from 699 vertebrate messenger RNAs. Nucleic Acids Research 15(20):8125–8148.

Kradin, R.L. et al. (1989) Tumour–infiltrating lymphocytes and interleukin–2 in treatment of advanced cancer. Lancet 577–580.

Kuzumaki, N. et al. (1979) Viral Expression and Immunogenicity of CBA mammary carcinomas and their hybrid lines with an L–cell derivative (A9HT)*. Eur. J. Cancer 15:1253–1261.

Lampson, L.A. et al. (1983) Striking paucity of HLA–A, B, C and $\beta_2$–microglobulin on human neuroblastoma cell lines. J. Immunol. 130:2471–2476.

Lew, D., et al. (1995) Cancer gene therapy using plasmid DNA: pharmacokinetic study of DNA following injection in mice. Human Gene Therapy 6:553–564.

Lindahl, P. et al. (1973) Enhancement by interferon of the expression of surface antigens on murine leukemia L 1210 cells. Proc. Natl. Acad. Sci. USA 70:2785–2788.

Lindahl, P. et al. (1976) Interferon treatment of mice: Enhanced expression of histocompatibility antigens on lymphoid cells. Proc. Natl. Acad. Sci. USA 73:1284–1287.

Lindenmann, J. et al. (1967) Viral oncolysis: Increased immunogenicity of host cell antigen associated with influenza virus. J. Exp. Med. 126:93–108.

Ljunggren, H.G. et al. (1986) Variations in MHC antigen expression on tumours and its significance; experimental strategies and interpretations in the analysis of changes in MHC gene expression during tumour progression; opposing influences of T cell and natural killer mediated resistance? J. Immunogenet. 13:141–151.

Lotze, M.T. et al. (1981) Lysis of fresh and cultured autologous tumor by human lymphocytes cultured in T–cell growth factor. Cancer Res. 41:4420–4425.

Lotze, M.T. et al. (1985) In vivo administration of purified human interleukin 2. II. Half life, immunologic effects, and expansion of peripheral lymphoid cells in vivo with recombinant IL2. J. Immunol. 135:2865–2875.

Mahon, K.A. et al. (1988) Prenatal lethality in a transgenic mouse line is the result of a chromosomal translocation. Proc. Natl. Acad. Sci. USA 85:1165–1168.

Marcelletti, J. et al. (1978) Spontaneous regression of friend virus–induced erythroleukemia. III. The role of macrophages in regression. J. Immunol. 120:1–8.

Mifflin, R., et al. (1991) Coupled transcription–polyadenylation in a cell–free system. The Journal of Biological Chemistry 266(29):19593–19598.

Morton, Donald L. et al. (1974) BCG immunotherapy of malignant melanoma: Summary of a seven–year experience. Ann. Surg. 180:635–643.

Mulé, James J. et al. (1989) IL–4 regulation of murine lymphokine–activated killer activity in vitro. Effects on the IL–2–induced expansion, cytotoxicity, and phenotype of lymphokine–activated killer effectors. J. Immunol. 142:726–733.

Nabel, E., et al. (1992) Gene transfer in vivo with DNA–liposome complexes: lack of autoimmunity and gonadal localization. Human Gene Therapy 3:649–656.

Nabel, Elizabeth G. et al. (1993) Recombinant platelet–derived growth factor B gene expression in porcine arteries induces intimal hyperplasia in vivo. J. Clin. Invest. 91:1822–1829.

Nabel, Elizabeth G. et al. (1989) Recombinant gene expression in vivo within endothelial cells of the arterial wall. Science 244:1342–1344.

Nabel, Elizabeth G. et al. (1990) Site–specific gene expression in vivo by direct gene transfer into the arterial wall. Science 249:1285–1288.

Nabel, Elizabeth G. et al. (1992) Transduction of a foreign histocompatibility gene into the arterial wall induces vasculitis. Proc. Natl. Acad. Sci. USA 89:5157–5161.

Nabel, G., et al. (1993) Direct gene transfer with DNA–liposome complexes in melanoma: expression, biologic activity, and lack of toxicity in humans. Proc. Natl. Acad. Sci. 90:11307–11311.

Nabel, Gary et al. (1987) An inducible transcription factor activates expression of human immunodeficiency virus in T cells. Nature 326:711–713.

Nabel, G., et al. (1994) Immunotherapy for cancer by direct gene transfer into tumors. Human Gene Therapy 5:57–77.

Nabel, Gary J. et al. (1992) Immunotherapy of malignancy by in vivo gene transfer into tumors. Hum. Gene. Ther. 3:399–410.

Nabel, Gary J. et al (1992) Response to the points to consider for immunotherapy of malignancy by in vivo gene transfer into tumors. Hum. Gene Ther. 3:705–711.

Old, Lloyd J. (1987) Polypetide mediator network Nature 326:330–331.

Old, Lloyd J. (1985) Tumor Necrosis Factor (TNF). Science 230:630–632.

Oldham, Robert K. (1983) Natural killer cells: Artifact to reality: An odyssey in biology. Canc. Metast. Rev. 2:323–336.

Overbeek, Paul A. et al. (1986) Tissue–specific expression in transgenic mice of a fused gene containing RSV terminal sequences. Science 231:1574–1577.

Phillips, Joseph H. et al. (1986) Dissection of the lymphokine–activated killer phenomenon. Relative contribution of peripheral blood natural killer cells and T lymphocytes to cytolysis. J. Exp. Med. 164:814–825.

Plautz, Gregory et al. (1991) Introduction of vascular smooth muscle cells expressing recombinant genes in vivo. Circ. 83:578–583.

Plautz, Gregory E. et al. (1993) Immunotherapy of malignancy by in vivo gene transfer into tumors. Proc. Natl. Acad. Sci. USA 90:4645–4649.

Powell, Marianne B. et al. (1985) The differential inhibitory effect of lymphotoxin and immune interferon on normal and malignant lymphoid cells. Lymphokin Res. 4:13–26.

Ralph, Peter et al. (1988) Role of interleukin 2, interleukin 4, and α, β, and γ interferon in stimulating macrophage antibody–dependent tumoricidal activity. J. Exp. Med. 167:712–717.

Rosenberg, S.A. et al. (1989) Experience with the use of high–dose interleukin–2 in the treatment of 652 cancer patients. Ann. Sug. 210:474–485.

Rosenberg, S.A. et al. (1985) Regression of established pulmonary metastases and subcutaneous tumor mediated by the systemic administration of high–does recombinant interleukin 2. J. Exp. Med. 161:1169–1188.

Rosenberg, S.A. et al. (1987) A progress report on the treatment of 157 patients with advanced cancer using lymphokine–activated killer cells and interleukin–2 or high–dose interleukin–2 alone. N. Eng. J. Med. 316:889–897.

Rosenberg, S.A. et al. (1988) Use of tumor–infiltrating lymphocytes and interleukin–2 in the immunotherapy of patients with metastatic melanoma, a preliminary report. N. Eng. J. Med. 319:1676–1680.

Rosenberg, S.A. et al. (1990) Gene transfer into humans—immunotherapy of patients with advanced melanoma, using tumor–infiltrating lymphocytes modified by retroviral gene transduction. N. Eng. J. Med. 323:570–578.

Rosenberg, S.A. et al. (1986) A new approach to the adoptive immunotherapy of cancer with tumor–infiltrating lymphocytes. Science 233:1318–1321.

Rosenberg, S.A. (1992) Immunization of cancer patients using autologous cancer cells modified by insertion of the gene for tumor necrosis factor. Hum. Gene Ther. 3:57–73.

Rosenberg, S.A. (1988) Immunotherapy of cancer using interleukin 2: Current status and future prospects. Immunol. Today 9:58–62.

Rubin J., et al. (1994) Phase I study of immunotherapy of hepatic metastases of colorectal carcinoma by direct gene transfer. Human Gene Therapy 5:1385–1399.

San, H., et al. (1993) Safety and short–term toxicity of a novel cationic lipid formulation for human gene therapy. Human Gene Therapy 4:781–788.

Schirrmacher, Volker et al. (1987) Prevention of metastatic spread by postoperative immunotherapy with virally modified autologous tumor cells. II. Establishment of specific systemic anti–tumor immunity. Clin. Exp. Metastasis 5:147–156.

Schmidt, Wilhelm et al. (1981) Variation of expression of histocompatibility antigens on tumor cells: Absence of $H-2K^k$–gene products from a gross–virus–induced leukemia in BALB.K. Immunogen. 14:323–339.

Shimizu, Yoshio et al. (1984) The augmentation of tumor–specific immunity by virus help. II. Enhanced induction of cytotoxic T lymphocyte and antibody responses to tumor antigens by vaccinia virus–reactive helper T cells. Eur. J. Immunol. 14:839–843.

Shu, Suyu et al. (1985) Adoptive immunotherapy of newly induced murine sarcomas. Cancer Res. 45:1657–1662.

Spiess, Paul J. et al. (1987) In vivo antitumor activity of tumor–infiltrating lymphocytes expanded in recombinant interleukin–2. J. Natl. Can. Inst. 79:1067–1075.

Stewart, Mark J. et al. (1992) Gene transfer in vivo with DNA–liposome complexes: Safety and acute toxicity in mice. Hum. Gene Ther. 3:267–275.

Talmadge, J.E. et al. (1985) Tumor growth and metastasis of B16–BL6 tumors following transfection of an allogeneic major histocompatibility complex ($D^d$) antigen. Proc. Amer. Assoc. for Cancer Res. 26:59.

Tanaka, K. et al. (1985) Reversal of oncogenesis by the expression of a major histocompatibility complex class I gene. Science 228:26–30.

Tepper, R.I. et al. (1989) Murine interleukin–4 displays potent anti–tumor activity in vivo. Cell 57:503–512.

Vogelzang, N., et al. (1994) Phase I study of immunotherapy of metastatic renal cell carcinoma by direct gene transfer into metastatic lesions. Human Gene Therapy 5:1357–1370.

Wallich, R. et al. (1985) Abrogation of metastatic properties of tumour cells by de novo expression of H–2K antigens following H–2 gene transfection. Nature 315:301–305.

Watanabe, Y. (1992) Transfection of interferon–γ in animal tumors—a model for local cytokine production and tumor immunity. Cancer Biology 3:43–46.

Watkins, J.F. et al. (1969) Immunization of mice against Ehrlich ascites tumour using a hamster/Ehrlich ascites tumour hybrid cell line. Nature 223:1018–1022.

Westphal, H. et al. (1985) Promoter sequences of murine αA crystallin, murine α2(I) collagen or of avian sarcoma virus genes linked to the bacterial chloramphenicol acetyl transferase gene direct tissue–specific patterns of chloramphenicol acetyl transferase expression in transgenic mice. Cold Spring Harb. Symp. Quant. Biol. 50:411–416.

Wood, C., et al. (1991) An internal ribosome binding site can be used to select for homologous recombinants at an immunoglobulin in heavy–chain locus. Proc. Natl. Acad. Sci. 88:8006–8010.

Yamaguchi, H. et al. (1982) Increased or decreased immunogenicity of tumor–associated antigen according to the amount of virus–associated antigen in rat tumor cells infected with friend virus. Cancer Immunol. Immunother. 12:119–123.

Yoshimura, K., et al. (1992) Expression of the human cystic fibrosis transmembrane conductance regulator gene in the mouse lung after in vivo intratracheal plasmid–mediated gene transfer. Nucleic Acids Research 20(12):3233–3240.

Yoshizawa, Hirohisa et al. (1991) Specific adoptive immunotherapy mediated by tumor–draining lymph node cells sequentially activated with anti–CD3 and IL–2. J. Immunol. 147:729–737.

Yron, Ilana et al. (1980) In vitro growth of murine T cells. V. The isolation and growth of lymphoid cells infiltrating syngeneic solid tumors. J. Immunol. 125:238–245.

Zbar, Berton et al. (1971) Suppression of tumor growth at the site of infection with living bacillus calmette–guérin. J. Natl. Canc. Inst. 46:831–839.

Marshall, E. (1995) Science 269:1050–1055.

Miller et al (1995) FASEB J. 9:190–199.

Gao et al (1991) Biochem. Biophys Res. Commun. 179:280–285.

Wood et al (1991) Proc. Natl. Acad. Sci. USA 88:8006–8010.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 4965 base pairs
        (B) TYPE: nucleic acid
        (C) STRANDEDNESS: double
        (D) TOPOLOGY: circular (ii) MOLECULE TYPE: cDNA (iii) HYPOTHETICAL: NO (iv) ANTI-SENSE: NO (v) FRAGMENT TYPE:

(vii) IMMEDIATE SOURCE:
        (B) CLONE: HLA-B7 and Beta-2

(xi) SEQUENCE DESCRIPTION: SEQ ID NO:1:

```
CTGCTCCCTG CTTGTGTGTT GGAGGTCGCT GAGTAGTGCG CGAGCAAAAT TTAAGCTACA      60

ACAAGGCAAG GCTTGACCGA CAATTGCATG AAGAATCTGC TTAGGGTTAG GCGTTTTGCG     120

CTGCTTCGCG ATGTACGGGC CAGATATACG CGTATCTGAG GGGACTAGGG TGTGTTTAGG     180

CGAAAAGCGG GGCTTCGGTT GTACGCGGTT AGGAGTCCCC TCAGGATATA GTAGTTTCGC     240

TTTTGCATAG GGAGGGGGAA ATGTAGTCTT ATGCAATACT CTTGTAGTCT TGCAACATGG     300

TAACGATGAG TTAGCAACAT GCCTTACAAG GAGAGAAAAA GCACCGTGCA TGCCGATTGG     360

TGGAAGTAAG GTGGTACGAT CGTGCCTTAT TAGGAAGGCA ACAGACGGGT CTGACATGGA     420

TTGGACGAAC CACTGAATTC CGCATTGCAG AGATATTGTA TTTAAGTGCC TAGCTCGATA     480

CTCTAGACGC CATTTGACCA TTCACCACAT TGGTGTGCAC CTCCAAGCTT CACCATGGTG     540

GTCATGGCGC CCCGAACCGT CCTCCTGCTG CTCTCGGCGG CCCTGGCCCT GACCGAGACC     600

TGGGCCGGCT CCCACTCCAT GAGGTATTTC TACACCTCCG TGTCCCGGCC CGGCCGCGGG     660

GAGCCCCGCT TCATCTCAGT GGGCTACGTG GACGACACCC AGTTCGTGAG GTTCGACAGC     720

GACGCCGCGA GTCCGAGAGA GGAGCCGCGG GCGCCGTGGA TAGAGCAGGA GGGGCCGGAG     780

TATTGGGACC GGAACACACA GATCTACAAG GCCCAGGCAC AGACTGACCG AGAGAGCCTG     840

CGGAACCTGC GCGGCTACTA CAACCAGAGC GAGGCCGGGT CTCACACCCT CCAGAGCATG     900

TACGGCTGCG ACGTGGGGCC GGACGGGCGC CTCCTCCGCG GCATGACCA GTACGCCTAC      960

GACGGCAAGG ATTACATCGC CCTGAACGAG GACCTGCGCT CCTGGACCGC CGCGGACACG    1020

GCGGCTCAGA TCACCCAGCG CAAGTGGGAG GCGGCCCGTG AGGCGGAGCA GCGGAGAGCC    1080

TACCTGGAGG GCGAGTGCGT GGAGTGGCTC CGCAGATACC TGGAGAACGG GAAGGACAAG    1140

CTGGAGCGCG CTGACCCCCC AAAGACACAC GTGACCCACC ACCCCATCTC TGACCATGAG    1200
```

```
GCCACCCTGA GGTGCTGGGC CCTGGGTTTC TACCCTGCGG AGATCACACT GACCTGGCAG    1260

CGGGATGGCG AGGACCAAAC TCAGGACACT GAGCTTGTGG AGACCAGACC AGCAGGAGAT    1320

AGAACCTTCC AGAAGTGGGC AGCTGTGGTG GTGCCTTCTG GAGAAGAGCA GAGATACACA    1380

TGCCATGTAC AGCATGAGGG GCTGCCGAAG CCCCTCACCC TGAGATGGGA GCCGTCTTCC    1440

CAGTCCACCG TCCCCATCGT GGGCATTGTT GCTGGCCTGG CTGTCCTAGC AGTTGTGGTC    1500

ATCGGAGCTG TGGTCGCTGC TGTGATGTGT AGGAGGAAGA GTTCAGGTGG AAAAGGAGGG    1560

AGCTACTCTC AGGCTGCGTG CAGCGACAGT GCCCAGGGCT CTGATGTGTC TCTCACAGCT    1620

TGAAAAGCCT GAGACAGCTG TCTTGTGAGG GACTGAGATG CAGGATTTCT TCACGCCTCC    1680

CCTTTGTGAC TTCAAGAGCC TCTGGCATCT CTTTCTGCAA AGGCACCTGA ATGTGTCTGC    1740

GTCCCTGTTA GCATAATGTG AGGAGGTGGA GAGACAGCCC ACCCTTGTGT CCACTGTGAC    1800

CCCTGTTCCC ATGCTGACCT GTGTTTCCTC CCCAGTCATC TTTCTTGTTC CAGGTCGAGA    1860

TCTCGACGGT ATCGATAAGC TTGATATCGA ATTCCGCCCC CCCCCCCCCC CCCTAACGTT    1920

ACTGGCCGAA GCCGCTTGGA ATAAGGCCGG TGTGCGTTTG TCTATATGTT ATTTTCCACC    1980

ATATTGCCGT CTTTTGGCAA TGTGAGGGCC CGGAAACCTG GCCCTGTCTT CTTGACGAGC    2040

ATTCCTAGGG GTCTTTCCCC TCTCGCCAAA GGAATGCAAG GTCTGTTGAA TGTCGTGAAG    2100

GAAGCAGTTC CTCTGGAAGC TTCTTGAAGA CAAACAACGT CTGTAGCGAC CCTTTGCAGG    2160

CAGCGGAACC CCCCACCTGG CGACAGGTGC CTCTGCGGCC AAAAGCCACG TGTATAAGAT    2220

ACACCTGCAA AGGCGGCACA ACCCCAGTGC CACGTTGTGA GTTGGATAGT TGTGGAAAGA    2280

GTCAAATGGC TCTCCTCAAG CGTATTCAAC AAGGGGCTGA AGGATGCCCA GAAGGTACCC    2340

CATTGTATGG GATCTGATCT GGGGCCTCGG TGCACATGCT TTACATGTGT TTAGTCGAGG    2400

TTAAAAAAAC GTCTAGGCCC CCCGAACCAC GGGGACGTGG TTTTCCTTTG AAAAACACGA    2460

TGATAATATG GCCACAACCA TGGCTCGCTC CGTGGCCTTA GCTGTGCTCG CGCTACTCTC    2520

TCTTTCTGGC CTGGAGGCTA TCCAGCGTAC TCCAAAGATT CAGGTTTACT CACGTCATCC    2580

AGCAGAGAAT GGAAAGTCAA ATTTCCTGAA TTGCTATGTG TCTGGGTTTC ATCCATCCGA    2640

CATTGAAGTT GACTTACTGA AGAATGGAGA GAGAATTGAA AAAGTGGAGC ATTCAGACTT    2700

GTCTTTCAGC AAGGACTGGT CTTTCTATCT CTTGTACTAC ACTGAATTCA CCCCCACTGA    2760

AAAAGATGAG TATGCCTGCC GTGTGAACCA TGTGACTTTG TCACAGCCCA AGATAGTTAA    2820

GTGGGATCGA GACATGTAAG CAGCATCATA AGCTTGAGG GATCCTAGAG CTCGCTGATC    2880

AGCCTCGACT GTGCCTTCTA GTTGCCAGCC ATCTGTTGTT TGCCCCTCCC CCGTGCCTTC    2940

CTTGACCCTG GAAGGTGCCA CTCCCACTGT CCTTTCCTAA TAAAATGAGG AAATTGCATC    3000

GCATTGTCTG AGTAGGTGTC ATTCTATTCT GGGGGGTGGG GTGGGCAGG ACAGCAAGGG    3060

GGAGGATTGG GAAGACAATA GCAGGCATGC TGGGGATGCG GTGGGCTCTA TGGCTTCTGA    3120

GGCGGAAAGA ACCAGCTGGG GCTCGAAATT CTTAGAAAAA CTCATCGAGC ATCAAATGAA    3180

ACTGCAATTT ATTCATATCA GGATTATCAA TACCATATTT TGAAAAAGC CGTTTCTGTA    3240

ATGAAGGAGA AAACTCACCG AGGCAGTTCC ATAGGATGGC AAGATCCTGG TATCGGTCTG    3300

CGATTCCGAC TCGTCCAACA TCAATACAAC CTATTAATTT CCCCTCGTCA AAAATAAGGT    3360

TATCAAGTGA GAAATCACCA TGAGTGACGA CTGAATCCGG TGAGAATGGC AAAAGCTTAT    3420

GCATTTCTTT CCAGACTTGT TCAACAGGCC AGCCATTACG CTCGTCATCA AAATCACTCG    3480

CATCAACCAA ACCGTTATTC ATTCGTGATT GCGCCTGAGC GAGACGAAAT ACGCGATCGC    3540

TGTTAAAAGG ACAATTACAA ACAGGAATCG AATGCAACCG GCGCAGGAAC ACTGCCAGCG    3600
```

-continued

```
CATCAACAAT ATTTTCACCT GAATCAGGAT ATTCTTCTAA TACCTGGAAT GCTGTTTTCC    3660

CGGGGATCGC AGTGGTGAGT AACCATGCAT CATCAGGAGT ACGGATAAAA TGCTTGATGG    3720

TCGGAAGAGG CATAAATTCC GTCAGCCAGT TTAGTCTGAC CATCTCATCT GTAACATCAT    3780

TGGCAACGCT ACCTTTGCCA TGTTTCAGAA ACAACTCTGG CGCATCGGGC TTCCCATACA    3840

ATCGATAGAT TGTCGCACCT GATTGCCCGA CATTATCGCG AGCCCATTTA TACCCATATA    3900

AATCAGCATC CATGTTGGAA TTTAATCGCG GCCTCGAGCA AGACGTTTCC CGTTGAATAT    3960

GGCTCATAAC ACCCCTTGTA TTACTGTTTA TGTAAGCAGA CAGTTTTATT GTTCATGACC    4020

AAAATCCCTT AACGTGAGTT TTCGTTCCAC TGAGCGTCAG ACCCCGTAGA AAGATCAAA    4080

GGATCTTCTT GAGATCCTTT TTTTCTGCGC GTAATCTGCT GCTTGCAAAC AAAAAAACCA    4140

CCGCTACCAG CGGTGGTTTG TTTGCCGGAT CAAGAGCTAC CAACTCTTTT TCCGAAGGTA    4200

ACTGGCTTCA GCAGAGCGCA GATACCAAAT ACTGTCCTTC TAGTGTAGCC GTAGTTAGGC    4260

CACCACTTCA AGAACTCTGT AGCACCGCCT ACATACCTCG CTCTGCTAAT CCTGTTACCA    4320

GTGGCTGCTG CCAGTGGCGA TAAGTCGTGT CTTACCGGGT TGGACTCAAG ACGATAGTTA    4380

CCGGATAAGG CGCAGCGGTC GGGCTGAACG GGGGGTTCGT GCACACAGCC CAGCTTGGAG    4440

CGAACGACCT ACACCGAACT GAGATACCTA CAGCGTGAGC TATGAGAAAG CGCCACGCTT    4500

CCCGAAGGGA GAAAGGCGGA CAGGTATCCG GTAAGCGGCA GGGTCGGAAC AGGAGAGCGC    4560

ACGAGGGAGC TTCCAGGGGG AAACGCCTGG TATCTTTATA GTCCTGTCGG GTTTCGCCAC    4620

CTCTGACTTG AGCGTCGATT TTTGTGATGC TCGTCAGGGG GGCGGAGCCT ATGGAAAAAC    4680

GCCAGCAACG CGGCCTTTTT ACGGTTCCTG GCCTTTTGCT GGCCTTTTGC TCACATGTTC    4740

TTTCCTGCGT TATCCCCTGA TTCTGTGGAT AACCGTATTA CCGCCTTTGA GTGAGCTGAT    4800

ACCGCTCGCC GCAGCCGAAC GACCGAGCGC AGCGAGTCAG TGAGCGAGGA AGCGGAAGAG    4860

CGCCTGATGC GGTATTTTCT CCTTACGCAT CTGTGCGGTA TTTCACACCG CATATGGTGC    4920

ACTCTCAGTA CAATCTGCTC TGATGCCGCA TAGTTAAGCC AGTAT                    4965
```

(2) INFORMATION FOR SEQ ID NO:2:

(i) SEQUENCE CHARACTERISTICS:
        (A) LENGTH: 4059 base pairs
        (B) TYPE: nucleic acid
        (C) STRANDEDNESS: double
        (D) TOPOLOGY: circular (ii) MOLECULE TYPE: cDNA (iii) HYPOTHETICAL: NO (iv) ANTI-SENSE: NO (v) FRAGMENT TYPE:

(vii) IMMEDIATE SOURCE:
        (B) CLONE: HLA-B7

(xi) SEQUENCE DESCRIPTION: SEQ ID NO:2:

```
CTGGTAACAG GATTAGCAGA GCGAGGTATG TAGGCGGTGC TACAGAGTTC TTGAAGTGGT     60

GGCCTAACTA CGGCTACACT AGAAGGACAG TATTTGGTAT CTGCGCTCTG CTGAAGCCAG    120

TTACCTTCGG AAAAAGAGTT GGTAGCTCTT GATCCGGCAA ACAAACCACC GCTGGTAGCG    180

GTGGTTTTTT TGTTTGCAAG CAGCAGATTA CGCGCAGAAA AAAAGGATCT CAAGAAGATC    240

CTTTGATCTT TTCTACGGGG TCTGACGCTC AGTGGAACGA AAACTCACGT TAAGGGATTT    300

TGGTCATGAA CAATAAAACT GTCTGCTTAC ATAAACAGTA ATACAAGGGG TGTTATGAGC    360
```

```
CATATTCAAC GGGAAACGTC TTGCTCGAGG CCGCGATTAA ATTCCAACAT GGATGCTGAT    420
TTATATGGGT ATAAATGGGC TCGCGATAAT GTCGGGCAAT CAGGTGCGAC AATCTATCGA    480
TTGTATGGGA AGCCCGATGC GCCAGAGTTG TTTCTGAAAC ATGGCAAAGG TAGCGTTGCC    540
AATGATGTTA CAGATGAGAT GGTCAGACTA AACTGGCTGA CGGAATTTAT GCCTCTTCCG    600
ACCATCAAGC ATTTTATCCG TACTCCTGAT GATGCATGGT TACTCACCAC TGCGATCCCC    660
GGGAAAACAG CATTCCAGGT ATTAGAAGAA TATCCTGATT CAGGTGAAAA TATTGTTGAT    720
GCGCTGGCAG TGTTCCTGCG CCGGTTGCAT TCGATTCCTG TTTGTAATTG TCCTTTTAAC    780
AGCGATCGCG TATTTCGTCT CGCTCAGGCG CAATCACGAA TGAATAACGG TTTGGTTGAT    840
GCGAGTGATT TTGATGACGA GCGTAATGGC TGGCCTGTTG AACAAGTCTG GAAAGAAATG    900
CATAAGCTTT TGCCATTCTC ACCGGATTCA GTCGTCACTC ATGGTGATTT CTCACTTGAT    960
AACCTTATTT TTGACGAGGG GAAATTAATA GGTTGTATTG ATGTTGGACG AGTCGGAATC   1020
GCAGACCGAT ACCAGGATCT TGCCATCCTA TGGAACTGCC TCGGTGAGTT TTCTCCTTCA   1080
TTACAGAAAC GGCTTTTTCA AAAATATGGT ATTGATAATC CTGATATGAA TAAATTGCAG   1140
TTTCATTTGA TGCTCGATGA GTTTTTCTAA GAATTGATCC AGACATGATA AGATACATTG   1200
ATGAGTTTGG ACAAACCACA ACTAGAATGC AGTGAAAAAA ATGCTTTATT TGTGAAATTT   1260
GTGATGCTAT TGCTTTATTT GTAACCATTA TAAGCTGCAA TAAACAAGTT AACAACAACA   1320
ATTGCATTCA TTTTATGTTT CAGGTTCAGG GGGAGGTGTG GGAGGTTTTT TAAAGCAAGT   1380
AAAACCTCTA CAAATGTGGT ATGGCTGATT ATTGGAATCT AAAATACACA AACAATTAGA   1440
ATCAGTAGTT TAACACATTA TACACTTAAA AATTTTATAT TTACCTTAGA GCTTTAAATC   1500
TCTGTAGGTA GTTTGTCCAA TTATGTCACA CCACAGAAGT AAGGTTCCTT CACAAAGATC   1560
TCGACCTGGA ACAAGAAAGA TGACTGGGGA GGAAACACAG GTCAGCATGG AACAGGGGT    1620
CACAGTGGAC ACAAGGGTGG GCTGTCTCTC CACCTCCTCA CATTATGCTA ACAGGGACGC   1680
AGACACATTC AGGTGCCTTT GCAGAAAAGA GTCCAGAGGC TCTTGAAGTC GCAAAGGGGA   1740
GGCGTGAAGA AATCCTGCAT CTCAGTCCCT CACAAGACAG CTGTCTCAGG CTTTTCAAGC   1800
TGTGAGAGAC ACATCAGAGC CCTGGGCACT GTCGCTGCAC GCAGCCTGAG AGTAGCTCCC   1860
TCCTTTTCCA CCTGAACTCT TCCTCCTACA CATCACAGCA GCGACCACAG CTCCGATGAC   1920
CACAACTGCT AGGACAGCCA GGCCAGCAAC AATGCCCACG ATGGGACGG TGGACTGGGA    1980
AGACGGCTCC CATCTCAGGG TGAGGGGCTT CGGCAGCCCC TCATGCTGTA CATGGCATGT   2040
GTATCTCTGC TCTTCTCCAG AAGGCACCAC CACAGCTGCC CACTTCTGGA AGGTTCTATC   2100
TCCTGCTGGT CTGGTCTCCA CAAGCTCAGT GTCCTGAGTT TGGTCCTCGC CATCCCGCTG   2160
CCAGGTCAGT GTGATCTCCG CAGGGTAGAA ACCCAGGGCC CAGCACCTCA GGGTGGCCTC   2220
ATGGTCAGAG ATGGGTGGT GGGTCACGTG TGTCTTTGGG GGGTCAGCGC GCTCCAGCTT    2280
GTCCTTCCCG TTCTCCAGGT ATCTGCGGAG CCACTCCACG CACTCGCCCT CCAGGTAGGC   2340
TCTCCGCTGC TCCGCCTCAC GGGCCGCCTC CCACTTGCGC TGGGTGATCT GAGCCGCGGT   2400
GTCCGCGGCG GTCCAGGAGC GCAGGTCCTC GTTCAGGGCG ATGTAATCCT TGCCGTCGTA   2460
GGCGTACTGG TCATGCCCGC GGAGGAGGCG CCCGTCCGGC CCCACGTCGC AGCCGTACAT   2520
GCTCTGGAGG GTGTGAGACC CGGCCTCGCT CTGGTTGTAG TAGCCGCGCA GGTTCCGCAG   2580
GCTCTCTCGG TCAGTCTGTG CCTGGGCCTT GTAGATCTGT GTGTTCCGGT CCCAATACTC   2640
CGGCCCCTCC TGCTCTATCC ACGGCGCCCG CGGCTCCTCT CTCGGACTCG CGGCGTCGCT   2700
GTCGAACCTC ACGAACTGGG TGTCGTCCAC GTAGCCCACT GAGATGAAGC GGGGCTCCCC   2760
```

-continued

```
GCGGCCGGGC CGGGACACGG AGGTGTAGAA ATACCTCATG GAGTGGGAGC GGCCCAGGTC    2820

TCGGTCAGGC CAGGGCGCCG AGAGCAGCAG GAGGACGGTT CGGGGCGCCA TGACCACCAT    2880

GGTGAAGCTT GGAGGTGCAC ACCAATGTGG TGAATGGTCA AATGGCGTTT ATTGTATCGA    2940

GCTAGGCACT TAAATACAAT TATCTCTGCA ATGCGGAATT CAGTGGTTCG TCCAATCCAT    3000

GTCAGACCTG TCTGTTGCCT TCCTAATAAG GCACGATCGT ACCACCTTAC TTCCACCAAT    3060

CGGCATGCAC GGTGCTTTTT CTCTCCTTGT AAGGCATGTT GCTAACTCAT CGTTACCATG    3120

TTGCAAGACT ACAAGTGTAT TGCATAAGAC TACATTTCCC CCTCCCTATG CAAAAGCGAA    3180

ACTACTATAT CCTGAGGGGA CTCCTAACCG CGTACAACCG AAGCCCCGCT TTTCGCCTAA    3240

ACACACCCTA GTCCCCTCAG ATACGCGTAT ATCTGGCCCG TACATCGCGA AGCAGCGCAA    3300

AACGCCTAAC CCTAAGCAGA TTCTTCATGC AATTGTCGGT CAAGCCTTGC CTTGTTGTAG    3360

CTTAAATTTT GCTCGCGCAC TACTCAGCGA CCTCCAACAC ACAAGCAGGG AGCAGATACT    3420

GGCTTAACTA TGCGGCATCA GAGCAGATTG TACTGAGAGT GCACCATATG CGGTGTGAAA    3480

TACCGCACAG ATGCGTAAGG AGAAAATACC GCATCAGGCG CTCTTCCGCT TCCTCGCTCA    3540

CTGACTCGCT GCGCTCGGTC GTTCGGCTGC GGCGAGCGGT ATCAGCTCAC TCAAAGGCGG    3600

TAATACGGTT ATCCACAGAA TCAGGGGATA ACGCAGGAAA GAACATGTGA GCAAAAGGCC    3660

AGCAAAAGGC CAGGAACCGT AAAAAGGCCG CGTTGCTGGC GTTTTTCCAT AGGCTCCGCC    3720

CCCCTGACGA GCATCACAAA AATCGACGCT CAAGTCAGAG GTGGCGAAAC CCGACAGGAC    3780

TATAAAGATA CCAGGCGTTT CCCCCTGGAA GCTCCCTCGT GCGCTCTCCT GTTCCGACCC    3840

TGCCGCTTAC CGGATACCTG TCCGCCTTTC TCCCTTCGGG AAGCGTGGCG CTTTCTCATA    3900

GCTCACGCTG TAGGTATCTC AGTTCGGTGT AGGTCGTTCG CTCCAAGCTG GGCTGTGTGC    3960

ACGAACCCCC CGTTCAGCCC GACCGCTGCG CCTTATCCGG TAACTATCGT CTTGAGTCCA    4020

ACCCGGTAAG ACACGACTTA TCGCCACTGG CAGCAGCCA                           4059
```

PLASMIDS SUITABLE FOR GENE THERAPY

The present application is a 371 of PCT/US94/06069, filed May 27, 1994 and a continuation-in-part of U.S. patent application No. Ser. No. 08/074,344 filed Jun. 7, 1993, now abandoned.

FIELD OF THE INVENTION

The present invention pertains to plasmids suitable for gene therapy and related methods.

BACKGROUND OF THE INVENTION

A variety of genetic abnormalities arise in human cancer that contribute to neoplastic transformation and malignancy. Instability of the genome generates mutations that alter cell proliferation, angiogenesis, metastasis, and tumor immunogenicity. Despite a better understanding of the molecular basis of cancer, many malignancies remain resistant to traditional forms of treatment. The definition of tumor-associated genetic mutations, however, has heightened interest in cancer as a target for gene therapy. Immunotherapy has shown promise as a primary approach to the treatment of malignancy. Indeed, specific cancers, such as melanoma or renal cell carcinoma, are relatively more responsive to modulation of immune function, possibly because the immune system can be induced to recognize mutant gene products in these cells. Conventionally, approaches to immunotherapy have involved the administration of non-specific immunomodulating agents such as Bacillus Calmette-Guerin (BCG), cytokines, and/or adoptive T cell transfer, which have shown promise in animal models (B. Zbar, et al., *J. Natl. Canc. Inst.* 46, 831 (1971); S. A. Rosenberg, et al., *J. Exp. Med.* 16, 1169 (1985); S. Shu, and S. A. Rosenberg, Cancer Res. 45, 1657 (1985); P. J. Spiess, et al., *J. Natl. Canc. Inst.* 79, 1067; T. Chou, et al., *J. Immunol.* 140, 2453 (1988); H. Yoshizawa, et al., *J. Immunol.* 147, 729 (1991)) and in man (D. L. Morton, et al., *Ann. Surg.* 180, 635 (1974); S. A. Rosenberg, et al., *Ann. Surg.* 210, 474 (1989); S. A. Rosenberg, et al., *N. Eng. J. Med.* 319, 1676 (1988); R. L. Kradin, et al., *Lancet* 577 (1989)). More recently, molecular genetic interventions have been designed in an attempt to improve the efficacy of immunotherapy. Human gene transfer protocols have been designed to monitor the traffic of lymphocytes into melanoma tumors (S. A. Rosenberg, et al., *N. Eng. J. Med.* 323, 570 (1990)) or to introduce cytokine genes into tumor cells to stimulate the host's immune response to residual tumor (S. A. Rosenberg, *Hum. Gene Ther.* 3, 57 (1992)).

Recently, a new molecular genetic intervention has been developed for human malignancy. This approach relies on the direct transmission of recombinant genes into established tumors in vivo to genetically modify them as they grow in situ. In animal models, introduction of a gene encoding a foreign major histocompatibility (MHC) protein (class I) in vivo signals the immune system to respond to the foreign antigen (G. E. Plautz, et al., *Proc. Natl. Acad. Sci. USA* 90, 4645 (1993); E. G. Nabel, et al., *Proc. Natl. Acad. Sci. USA* 89, 5157 (1992)). More importantly, when this gene is transduced into established tumors in vivo, a cytolytic T cell response is also generated against unmodified tumor cells. In murine models, this approach has led to significant reductions in tumor growth and, in some cases, complete remission (G. E. Plautz, et al., *Proc. Natl. Acad. Sci. USA* 90, 4645 (1993)). Based on these studies, approval was recently received from the Recombinant DNA Advisory Committee of the National Institutes of Health to conduct a human clinical protocol using direct transfer of a human transplantation antigen gene in an effort to treat malignancy. This protocol proposed to perform direct gene transfer in humans and to utilize a non-viral vector which reduces several safety concerns about viral vectors. This clinical trial involved the treatment of patients with metastatic melanoma at subcutaneous lesions. The treatment constituted intratumoral injection of the human class I MHC gene, HLA-B7, complexed to a cationic liposome, DC-Cholesterol (G. J. Nabel, *Hum. Gene Ther.* 3, 705 (1992); X. Gao and L. Huang, *Biochem. Biophys. Res. Commun.* 179, 280 (1991)). These patients received escalating doses of the DNA liposome complex. Recombinant gene expression, toxicity, and the immunologic response to treatment is being evaluated. Based on animal studies, no toxicities had been readily apparent using these modes of direct gene transfer in vivo in short-term or long-term studies (G. J. Nabel, *Hum. Gene Ther.* 3, 399 (1992); G. J. Nabel, *Hum. Gene Ther.* 3, 705 (1992); M. J. Stewart, et al., *Hum. Gene Ther.* 3, 267 (1992)). Taken together, these studies were intended to determine whether direct gene transfer was an appropriate form of treatment for malignancy.

Direct Gene Transfer and Modulation of the Immune System

The utilization of catheter-based gene delivery in vivo provided a model system for the introduction of recombinant gene-containing molecules into specific sites in vivo. Early studies focused on the demonstration that specific reporter genes could be expressed in vivo (E. G. Nabel, et al., *Science* 249, 1285 (1990); E. G. Nabel, et al., *Science* 244, 1342 (1989)). Subsequent studies were designed to determine whether specific biologic responses could be induced at sites of recombinant gene transfer. To address this question, a highly immunogenic molecule, a foreign major histocompatibility complex (MHC), was used to elicit an immune response in the iliofemoral artery using a porcine model. The human HLA-B7 gene was introduced using direct gene transfer with a retroviral vector or DNA liposome complex (E. G. Nabel, et al., *Proc. Natl. Acad. Sci. USA* 89, 5157 (1992)). With either delivery system, expression of the recombinant HLA-B7 gene product could be demonstrated at specific sites within the vessel wall. More importantly, the expression of this foreign histocompatibility antigen induced an immunologic response at the sites of genetic modification. This response included a granulomatous mononuclear cell infiltrate beginning 10 days after introduction of the recombinant gene. This response resolved by 75 days after gene transfer; however, a specific cytolytic T cell response against the HLA-B7 molecule was persistent. This study demonstrated that a specific immunologic response could be induced by the introduction of a foreign recombinant gene at a specific site in vivo. Moreover, this study provided one of the first indications that direct gene transfer of specific recombinant genes could elicit an immune response to the product of that gene in vivo (E. G. Nabel, et al., *Proc. Natl. Acad. Sci. USA* 89, 5157 (1992)).

These studies suggested that the introduction of the appropriate recombinant genes could be used to stimulate the immune system to recognize its product in vivo. In addition, this approach provided a general method for the induction of a specific site in vivo. To determine whether direct gene transfer might be appropriate for the treatment of disease, a murine model of malignancy was developed. Direct gene transfer of an allogeneic histocompatibility complex gene into a murine tumor was found to elicit an immune response not only to the foreign MHC protein but also to previously unrecognized tumor-associated antigens. These immune responses were T cell-dependent, and these tumor-associated proteins were recognized within the context of the self major histocompatibility complex. In animals presensitized to a specific MHC haplotype, direct gene transfer into established tumors could attenuate tumor growth or, in some cases, lead to complete tumor regression (G. E. Plautz, et al., *Proc. Natl. Acad. Sci. USA* 90, 4645 (1993)). These studies demonstrated that direct gene transfer of foreign MHC genes into tumors have potentially therapeutic effects that may be appropriate for the treatment of malignancy.

Immunotherapy of Malignancy

In some instances, the immune system appears to contribute to the surveillance and destruction of neoplastic cells, by mobilization of either cellular or humoral immune effectors. Cellular mediators of anti-tumor activity include MHC-restricted cytotoxic T cells, natural killer (NK) cells (R. K. Oldham, *Canc. Metast. Rev.* 2, 323 (1983); R. B. Herberman, *Concepts Immunopathol.* 1, 96 (1985)) and lymphokine-activated killer (LAK) cells (S. A. Rosenberg, *Immunol. Today* 9, 58 (1988)). Cytolytic T cells which infiltrate tumors have been isolated and characterized (I. Yron, et al., *J. Immunol.* 125, 238 (1980)). These tumor infiltrating lymphocytes (TIL) selectively lyse cells of the tumor from which they were derived (P. J. Spiess, et al., *J. Natl. Canc. Inst.* 79, 1067; S. A. Rosenberg, et al., *Science* 223, 1318 (1986)). Macrophages can also kill neoplastic cells through antibody-dependent mechanisms (J. Marcelletti and P. Furmanski, *J. Immunol.* 120, 1 (1978); P. Ralph, et al., *J. Exp. Med.* 167, 712 (1988)), or by activation induced by substances such as BCG (P. Alexander, *Natl. Cancer Inst. Monogr.* 39, 127 (1973)).

Cytokines can also participate in the anti-tumor response, either by a direct action on cell growth or by activating cellular immunity. The cytostatic effects of tumor necrosis factor-α (TNF-α) (L. J. Old, *Science* 230, 630 (1985)) and lymphotoxin (M. B. Powell, et al., *Lymphokin Res.* 4, 13 (1985)) can result in neoplastic cell death. Interferon-γ (IFN-γ) markedly increases class I MHC cell surface expression (P. Lindahl, et al., *Proc. Natl. Acad. Sci. USA* 70, 2785 (1973); P. Lindahl, et al., *Proc. Natl. Acad. Sci. USA* 73, 1284 (1976)) and synergizes with TNF-α in producing this effect (L. J. Old, *Nature* 326, 330 (1987)). Colony stimulating factors such as G-CSF and GM-CSF activate neutrophils and macrophages to lyse tumor cells directly (S. C. Clark and R. Kamen, *Science* 236, 1229 (1987)), and interleukin-2 (IL-2) activates Leu-19+ NK cells to generate lymphokine activated killer cells (LAK) capable of lysing autologous, syngeneic or allogeneic tumor cells but not normal cells (S. A. Rosenberg, *Immunol. Today* 9, 58 (1988); M. T. Lotze, et al., *Cancer Res.* 41, 4420 (1981); C. S. Johnson, et al., *Cancer Res.* 50, 5682 (1990)). The LAK cells lyse tumor cells without preimmunization or MHC restriction (J. H. Phillips and L. L. Lanier, *J. Exp. Med.* 164, 814 (1986)). Interleukin-4 (IL-4) also generates LAK cells and acts synergistically with IL-2 in the generation of tumor specific killers cells (J. J. Mule, et al., *J. Immunol.* 142, 726 (1989)).

Since most malignancies arise in immunocompetent hosts, it is likely that tumor cells have evolved mechanisms to escape host defenses, perhaps through evolution of successively less immunogenic clones (G. Klein and E. Klein, *Proc. Natl. Acad. Sci. USA* 74, 2121 (1977)). Several studies suggest that reduced expression of MHC molecules may provide a mechanism to escape detection by the immune system. Normally, the class I MHC glycoprotein is highly expressed on a wide variety of tissues and, in association with β-2 microglobulin, presents endogenously synthesized peptide fragments to CD8 positive T cells through specific interactions with the CD8/T-cell receptor complex (P. J. Bjorkman and P. Parham, *Ann. Rev. Biochem.* 59, 253 (1990). Deficient expression of class I MHC molecules could limit the ability of tumor cells to present antigens to cytotoxic T cells. Freshly isolated cells from naturally occurring tumors frequently lack class I MHC antigen completely or show decreased expression (C. A. Holden, et al., *J. Am. Acad. Dermatol.* 9, 867 (1983); N. Isakov, et al., *J. Natl. Canc. Inst.* 71, 139 (1983); W. Schmidt, et al., *Immunogen.* 14, 323 (1981); K. Funa, et al., *Lab Invest.* 55, 185 (1986); L. A. Lampson, et al., *J. Immunol.* 130, 2471 (1983)). Reduced class I MHC expression could also facilitate growth of these tumors when transplanted into syngeneic recipients. Several tumor cell lines which exhibit low levels of class I MHC proteins become less oncogenic when expression vectors encoding the relevant class I MHC antigen are introduced into them (K. Tanaka, et al., *Science* 228, 26 (1985); K. Hui, et al., *Nature* 311, 750 (1984); R. Wallich, et al., *Nature* 315, 301 (1985); H-G. Ljunggren and K. Karre, *J. Immunogenet.* 13, 141 (1986); G. J. Hammerling, et al., *J. Immunogenet.* 13, 153 (1986)). In some experiments, tumor cells which express a class I MHC gene confer immunity in naive recipients against the parental tumor (K. Hui and F. Grosveld, H. Festenstein, *Nature* 311, 750 (1984); R. Wallich, et al., *Nature* 315, 301 (1985)). The absolute level of class I MHC expression however, is not the only factor which influences the tumorigenicity or immunogenicity of tumor cells. In one study, mouse mammary adenocarcinoma cells, treated with 5-azacytidine and selected for elevated levels of class I MHC expression did not display altered tumorigenicity compared to the parent line (D. A. Carlow, et al., *J. Natl. Canc. Inst.* 81, 759 (1989)).

The immune response to tumor cells can be stimulated by systemic administration of IL-2 (M. T. Lotze, et al, *J. Immunol.* 135, 2865 (1985)), or IL-2 with LAK cells (S. A. Rosenberg, et al., *N. Eng. J. Med.* 316, 889 (1987); C. S. Johnson, et al., *Leukemia* 3, 91 (1989)). Clinical trials using tumor infiltrating lymphocytes are also in progress (S. A. Rosenberg, et al., *N. Eng. J. Med.* 323, 570 (1990)). Recently, several studies have examined the tumor suppressive effect of lymphokine production by genetically altered tumor cells. The introduction of tumor cells transfected with an IL-2 expression vector into syngeneic mice stimulated an MHC class I restricted cytolytic T lymphocyte response which protected against subsequent rechallenge with the parental tumor cell line (E. R. Fearon, et al., *Cell* 60, 397 (1990)). Expression of IL-4 by plasmacytoma or mammary adenocarcinoma cells induced a potent anti-tumor effect mediated by infiltration of eosinophils and macrophages (R. I. Tepper, et al., *Cell* 57, 503 (1989)). These studies demonstrate that cytokines, expressed at high local concentrations, are effective anti-tumor agents.

An alternative approach has recently been proposed to stimulate an anti-tumor response through the introduction of an allogeneic class I MHC gene into established human tumors (supra). The antigenicity of tumor cells had been altered previously by the expression of viral antigens through infection of tumor cells (J. Lindenmann and P. A. Klein, *J. Exp. Med.* 126, 93 (1967); Y. Shimizu, et al., *Eur. J. Immunol.* 14, 839 (1984); H. Yamaguchi, et al., *Cancer Immunol. Immunother.* 12, 119 (1982); M. Hosokama, *Cancer Res.* 43, 2301 (1983); V. Shirrmacher and R. Heicappell, *Clin. Exp. Metastasis* 5, 147 (1987)), or expression of allogeneic antigens introduced by somatic cell hybridization (J. F. Watkins and L. Chen, *Nature* 223, 1018 (1969); N. Kuzumaki, et al., *Eur. J. Cancer.* 15, 1253 (1979)). Allogeneic class I MHC genes had been introduced into tumor cells by transfection and subsequent selection in vitro. These experiments produced some conflicting results. In one case, transfection of an allogeneic class I MHC gene (H-2L$^d$) into an H-2$^b$ tumor resulted in immunologic rejection of the transduced cells and also produced transplantation resistance against the parent tumor cells (T. Itaya, et al., *Cancer Res.* 47, 3136 (1987)). In another instance, transfection of H-2$^b$ melanoma cells with the H-2D$^d$ gene did not lead to rejection (J. E. Talmadge, et al., *Proc. Amer. Assoc. for Cancer Res.* 26, 59 (1985)), however increased differential expression of H-2D products relative to H-2K may have affected the metastatic potential and immunogenicity of tumor cells (J. Gopas, et al., *Adv. Cancer Res.* 53, 89 (1989)). The effects of allogeneic H-2K gene expression in tumor cells was examined in another study (G. A. Cole, et al., *Proc. Natl. Acad. Sci. USA* 84, 8613 (1987)). Several subclones which were selected in vitro and expressed an allogeneic gene were rejected in mice syngeneic for the parental tumor line, however, other subclones did not differ from the parental, untransduced line in generating tumors. This finding suggests that clone-to-clone variation in in vivo growth and tumorigenic capacity may result in other modifications of cells, caused by transfection or the subcloning procedure, which affects their tumorigenicity. These types of clonal differences may be minimized by transducing a population of cells directly in vivo.

Gene Therapy Approaches

The immune system can provide protection against cancer and may play an important role as an adjuvant treatment for malignancy. Lymphokine activated killer cells (LAK) and tumor infiltrating lymphocytes (TIL) can lyse neoplastic cells and produce partial or complete tumor rejection. Expression of cytokine genes in malignant cells has also enhanced tumor regression. Because current strategies to stimulate an immune response against tumor cells often fail to eradicate tumors, an important goal of immunotherapy is to improve upon current techniques and understand the mechanisms of immune recognition.

A model has been described for the immunotherapy of malignancy using a gene encoding a transplantation antigen, an allogeneic class I major histocompatibility complex (MHC) antigen, introduced into human tumors in vivo by DNA/liposome transfection (G. J. Nabel, *Hum. Gene Ther.* 3, 399 (1992); G. J. Nabel, *Hum. Gene Ther.* 3, 705 (1992)). Expression of allogeneic MHC antigens on tumor cells stimulates immunity against both the allogeneic MHC gene on transduced cells as well as previously unrecognized antigens in unmodified tumor cells (G. E. Plautz, et al., *Proc. Natl. Acad. Sci. USA* 90, 4645 (1993)). The introduction of an allogeneic MHC gene directly into tumors in vivo has induced partial tumor regressions, as well as the specific cytotoxic T cell response to other antigens. In a recent trial in humans, no toxicity of this form of treatment was observed. It is an object of the present invention to optimize this gene therapy approach.

SUMMARY OF THE INVENTION

The invention provides a vector adapted for use in transferring into tissue or cells of an organism genetic material encoding one or more cistrons capable of expressing one or more immunogenic or therapeutic peptides, comprising one or more of the cistrons and a backbone that comprises the following elements: an origin of replication derived from pBR322; genetic material encoding a selectable marker that confers resistance to an antibiotic; a promoter operably linked to any of the cistrons, which promoter is derived from CMV or RSV LTR or RSV LTR in which a polyadenylation signal native to the RSV LTR has been mutated; and a polyadenylation signal that facilitates expression of any of the cistrons, which polyadenylation signal is derived from bovine growth hormone gene or SV40 or SV40 in which essentially all of any open reading frames native to the SV40 have been deleted; and wherein the backbone optionally further comprises one or more of the following elements: a ribosome binding site that facilitates translation of messages of any of the cistrons, which ribosome binding site is derived from EMC virus; translation initiation sequence that facilitates expression of any of the cistrons; and genetic material that facilitates splicing of transcripts of any of the cistrons.

In the vector, the genetic material that facilitates splicing may be derived from SV40 or SV40 in which essentially all of any open reading frames native to the SV40 have been deleted.

In the vector, the peptides may stimulate T-cell immunity against the tissue or cells. The peptides may comprise class I major histocompatibility complex (MHC) antigens, β-2 microglobulins, or cytokines. The MHC antigen may be foreign to the organism. The MHC antigen may be HLA-B7.

In the vector, DNA encoding the HLA-B7 may have an intron native to the HLA-B7 deleted.

The vector may have the nucleotide sequence set forth in SEQ ID NO:1.

The vector may have the nucleotide sequence set forth in SEQ ID NO:2.

In the vector, the transferring may occur in vitro. The transferring may occur in vivo. The in vivo transferring may be mediated by a catheter.

In the vector, the selectable marker may confer resistance to kanamycin, the promoter may be derived from RSV LTR in which a polyadenylation signal native to the RSV LTR has been mutated, and the polyadenylation signal may be derived from bovine growth hormone gene.

The vector may have that nucleotide sequence set forth in SEQ ID NO:1 which codes for: the origin of replication, the genetic material encoding a selectable marker, the promoter, the polyadenylation signal, the ribosome binding site, and the translation initiation sequence.

The vector may have a plurality of cistrons which are is organized in a poly-cistronic transcription unit, wherein the selectable marker confers resistance to kanamycin, wherein the promoter, which is operably linked to the poly-cistronic transcription unit, is derived from RSV LTR in which a polyadenylation signal native to the RSV LTR has been mutated, and wherein the polyadenylation signal, which facilitates processing of the poly-cistronic transcription unit, is derived from bovine growth hormone gene.

The vector may have two cistrons which are organized in a bi-cistronic transcription unit, wherein the selectable marker confers resistance to kanamycin, wherein the promoter, which is operably linked to the bi-cistronic transcription unit, is derived from RSV LTR in which a polyadenylation signal native to the RSV LTR has been mutated, and wherein the polyadenylation signal, which facilitates processing of the bi-cistronic transcription unit, is derived from bovine growth hormone gene.

The vector may have one cistron, wherein the selectable marker confers resistance to kanamycin, wherein the promoter, which is operably linked to the cistron, is derived from RSV LTR in which a polyadenylation signal native to the RSV LTR has been mutated, and wherein the polyadenylation signal, which facilitates expression of the cistron, is derived from bovine growth hormone gene.

The invention also provides a pharmaceutical composition comprising any of the vectors given above.

In the pharmaceutical composition, the vector may be in association with a transfer-facilitating vehicle. The vehicle may comprise a transfection-facilitating cationic lipid formulation. The cationic lipid formulation may be DMRIE-DOPE. The DMRIE-DOPE may have a molar ratio of 5:5. The vehicle may comprise an infection-facilitating viral vector.

The invention further provides a method for treating a disorder, in an organism, characterized as being responsive to the stimulation of T-cell immunity, comprising the step of transferring a vector into tissue or cells of the organism, wherein the vector comprises genetic material encoding one or more cistrons capable of expressing one or more peptides that stimulate T-cell immunity against the tissue or cells, such that the peptide or peptides are expressed resulting in the treatment of the disorder.

In the method, the disorder may be neoplastic disease. The neoplastic disease may be melanoma cancer. The vector may comprise any of the vectors given above. The transferring may occur in vitro. The transferring may occur in vivo. The in vivo transferring may be mediated by a catheter.

In the method, the vector may be associated with a transfer-facilitating vehicle. The vehicle may comprise a transfection-facilitating cationic lipid formulation. The cationic lipid formulation may be DMRIE-DOPE. The DMRIE-DOPE may have a molar ratio of 5:5. The vehicle may comprise an infection-facilitating viral vector.

The invention moreover provides a DNA cassette adapted for use in transferring into tissue or cells of an organism genetic material encoding one or more cistrons capable of expressing one or more immunogenic or therapeutic peptides or polypeptides, comprising the following elements: an origin of replication derived from pBR322; genetic material encoding a selectable marker that confers resistance to an antibiotic; a promoter operably linked to any of the cistrons, which promoter is derived from CMV or RSV LTR or RSV LTR in which a polyadenylation signal native to the RSV LTR has been mutated; and a polyadenylation signal that facilitates expression of any of the cistrons, which polyadenylation signal is derived from bovine growth hormone gene or SV40 or SV40 in which essentially all of any open reading frames native to the SV40 have been deleted; and wherein the DNA cassette optionally further comprises one or more of the following elements: a ribosome binding site that facilitates translation of messages of any of the cistrons, which ribosome binding site is derived from EMC virus; translation initiation sequence that facilitates expression of any of the cistrons; and genetic material that facilitates splicing of transcripts of any of the cistrons.

In the DNA cassette, the genetic material that facilitates splicing may be derived from SV40 or SV40 in which essentially all of any open reading frames native to the SV40 have been deleted.

In the DNA cassette, the selectable marker may confer resistance to kanamycin, the promoter may be derived from RSV LTR in which a polyadenylation signal native to the RSV LTR has been mutated, and the polyadenylation signal may be derived from bovine growth hormone gene.

The DNA cassette may have that nucleotide sequence set forth in SEQ ID NO:1 which codes for: the origin of replication, the genetic material encoding a selectable marker, the promoter, the polyadenylation signal, the ribosome binding site, and the translation initiation sequence.

The DNA cassette may have a plurality of cistrons which are organized in a poly-cistronic transcription unit, wherein the selectable marker confers resistance to kanamycin, wherein the promoter, which is operably linked to the polycistronic transcription unit, is derived from RSV LTR in which a polyadenylation signal native to the RSV LTR has been mutated, and wherein the polyadenylation signal, which facilitates processing of the poly-cistronic transcription unit, is derived from bovine growth hormone gene.

The DNA cassette may have two cistrons which are organized in a bi-cistronic transcription unit, wherein the selectable marker confers resistance to kanamycin, wherein the promoter, which is operably linked to the bi-cistronic transcription unit, is derived from RSV LTR in which a polyadenylation signal native to the RSV LTR has been mutated, and wherein the polyadenylation signal, which facilitates processing of the bi-cistronic transcription unit, is derived from bovine growth hormone gene.

The DNA cassette may have one cistron, wherein the selectable marker confers resistance to kanamycin, wherein the promoter, which is operably linked to the cistron, is derived from RSV LTR in which a polyadenylation signal native to the RSV LTR has been mutated, and wherein the polyadenylation signal, which facilitates expression of the cistron, is derived from bovine growth hormone gene.

The invention additionally provides a recombinant expression system comprising a host organism and a genetic construct having an origin of replication derived from pBR322; genetic material encoding a selectable marker that confers resistance to an antibiotic; one or more cistrons organized in a poly-cistronic, bi-cistronic, or uni-cistronic transcription unit, a promoter operably linked to the transcription unit which promoter is derived from CMV or RSV LTR or RSV LTR in which a polyadenylation signal native to the RSV LTR has been mutated, and a polyadenylation signal that facilitates processing of the transcription unit which polyadenylation signal is derived from bovine growth hormone gene or SV40 or SV40 in which essentially all of any open reading frames native to the SV40 have been deleted; and wherein the recombinant expression system optionally comprises one or more of the following elements: a ribosome binding site that facilitates translation of messages of any of the cistrons internal to the transcription unit which ribosome binding site is derived from EMC virus; translation initiation sequence that facilitates expression of any of the cistrons; and intron sequence that facilitates splicing of transcripts of any of the cistrons. In the recombinant expression system, the host organism may be a human.

DESCRIPTION OF THE PREFERRED EMBODIMENTS

The present invention relates to transfer of a human transplantation antigen to treat malignancy. It includes (1) modifications in vector design which enhance expression in vivo; (2) development of a more efficacious cationic liposome and other vehicles to improve efficiency of gene delivery; (3) optimization of gene delivery; and (4) application to different tumor cell types.

The anti-tumor immune response may be augmented by preimmunization and administration of cytokines, including tumor necrosis factor-α, interferon-γ, or interleukin-2, or used in combination with adoptive transfer or TIL therapy. The present invention provides an alternative strategy for the immunotherapy of malignancy and optimized vectors for use in such treatment. Adaptations of this method may also be applied to the treatment of other human diseases.

Vector Modifications

Vectors are provided that contain some or all of the modifications described herein designed to improve their efficacy and safety. Two such vectors are plasmids having the sequences set forth in SEQ ID NO:1 and SEQ ID NO:2. Additionally, the features characterizing these two vectors are summarized in Tables 1 and 2 infra. Moreover, the preparation of these two vectors is exemplified in Examples 1 and 2; other methods of preparation are known to those in the art.

TABLE 1 pHLA-B7/beta-2 microglobulin plasmid expression vector

| FEATURES | FROM | TO | DESCRIPTION |
|---|---|---|---|
| regulatory region | 1 | 529 | RSV 3' LTR Promoter |
| HLA-B7 heavy chain | 535 | 1853 | cDNA sequence |
| HLA-B7 coding sequence | 535 | 1620 | open reading frame |
| HLA-B7 signal peptide | 535 | 606 | predicted signal pep. |
| HLA-B7 mature peptide | 607 | 1620 | based on pred. pep. |
| synthetic linker | 1854 | 1888 | |
| EMCV internal ribosome entry | 1889 | 2479 | CAP independent translational enhancer |
| HLA-B7 light chain | 2480 | 2846 | β-2 microglobulin cDNA |
| light chain coding sequence | 2480 | 2836 | open reading frame |
| synthetic linker | 2847 | 2870 | |
| BGH 3' UTR and terminator | 2871 | 3111 | BGH transcription term. and poly A signal seq. |
| synthetic linker | 3112 | 3151 | |
| kanamycin resistance gene | 3152 | 4013 | Tn 903 |
| pBR322 | 4014 | 4965 | bacterial plasmid and prokaryotic ori. of rep. |

TABLE 2 pHLA-B7 plasmid expression vector

| FEATURES | FROM | TO | DESCRIPTION |
|---|---|---|---|
| pBR322 | 1 | 354 | bacterial plasmid and prokaryotic ori. of rep. |
| kanamycin resistance gene | 355 | 1170 | Tn 903 |
| poly A signal seq. | 1410 | 1177 | SV40 |
| intron | 1560 | 1412 | SV40 small t intron |
| HLA-B7 heavy chain | 2880 | 1561 | cDNA sequence |
| HLA-B7 3' UTR | 1794 | 1561 | 3' UTR region |
| HLA-B7 coding seq. | 2880 | 1795 | open reading frame |
| regulatory region | 3415 | 2886 | RSV 3' LTR promoter |
| pBR322 | 3416 | 4059 | bacterial plasmid |

The optimization of the vectors includes the incorporation of sequences encoding appropriate peptides and the tailoring of sites to maximize gene expression. A peptide is understood to be any translation product regardless of size, and whether or not post-translationally modified, as, for example, in glycosylation and phosphorylation.

In one experiment, the expression of HLA-B7 has been observed to be improved by the removal of a native intron and the addition of a consensus translation initiation sequence. See Example 3.

In another experiment, the inclusion of the β-2 microglobulin gene on the same vector as that encoding a class I MHC gene has been studied for synthesis of the complete histocompatibility molecule, which is composed of these two gene products. Ordinarily, these two chains are co-transported to the cell surface. Some human cancer cells do not express endogenous β-2 microglobulin, thus limiting their ability to stably express class I on the cell surface. We have found that the inclusion of the β-2 microglobulin gene on the same plasmid allows for expression in these otherwise resistant cells and improves expression in other cells, thus overcoming a potential mechanism of resistance. See Example 4.

A further modification of the vectors involves the expression of a cytokine gene in addition to class I MHC and β-2 microglobulin. The elaboration of cytokines such as IL-2 or GM-CSF could further stimulate T cell immunity against tumors locally and improve recognition of tumor-associated antigens. In experimental animal models, the introduction of IL-2 has allowed for improved anti-tumor efficacy (E. R. Fearon, et al., *Cell* 60, 397 (1990)). See Example 5.

Accordingly, in one embodiment of the invention, vectors are provided which are derived from viruses, and in a preferred embodiment, they are derived from bacterial plasmids. Plasmid vectors are likely to be at least as safe as standard viral vectors, as they will not be introduced into a packaging cell line thus precluding incorporation of other recombinant gene products into the delivery vehicle. Additionally, plasmid vectors may even be safer, since the delivery vehicle is unlikely to be inserted into the host genome hence reducing the potential for insertional mutagenesis. Moreover, cells which express genes encoding foreign histocompatibility antigens are to be eliminated by the host's immune system after several weeks in situ, minimizing any concerns regarding persistent expression of implanted genes in vivo. To maximize safety concerns, immunomodulating agents such as cytokines are preferably included on the same transcript as MHC antigens, linking the expression of the cytokine gene to expression of the foreign histocompatibility antigen, thus ensuring only transient expression of other exogenous sequences.

Optimization of plasmid vectors may be directed at any of the various stages in the life cycle of the plasmid, both in culture and in the animal, and both during transcription of genes and translation into peptides. In one embodiment of the invention, plasmid DNA is grown in a standard *E. coli* host strain, such as DH5α, DH10B, HB101, JM109, or XL1-Blue, until the final preparation for use in, for example, patients. Introduction of the plasmid DNA into the *E. coli* host cell is achieved, by, for instance, calcium chloride transfection or electroporation, where the plasmid replicates in an extrachromosomal form. Thus, in this embodiment, the plasmid contains an origin of replication that facilitates DNA synthesis in prokaryotes. (Other origins of replication that facilitate DNA synthesis in eukaryotes are contemplated in other embodiments wherein, for example, the vector is propagated in eukaryotic cells.) Such origins of replication suitable for growth in prokaryotes include, for example, those found on plasmid pBR322, plasmid ColE1, and pUC based plasmids. Applicants prefer the origin the replication derived from pBR322.

In another embodiment of the invention, vectors are provided that possess the ability to confer a readily selectable phenotypic trait on host cells that is used to select transformants. In a preferred embodiment, the selectable marker confers antibiotic resistance. Antibiotics, however, may cause adverse reactions in, for example, patients who may be exposed to residual amounts during the course of gene therapy. An antibiotic such as ampicillin is found, for instance, to precipitate anaphylactic shock and other allergic reactions when administered to those who are susceptible. Ampicillin also tends to decompose in culture, rendering it unsuitable for the selection of transformants. To preclude the loss of plasmids during in vitro propagation, wasteful amounts of ampicillin are inclined to be used. Accordingly, in this preferred embodiment, the selectable marker most preferred confers resistance to an antibiotic that is safe and cheap to use. Such antibiotics include neomycin, tetracycline, geneticin, chloramphenicol, spectinomycin, streptomycin, hygromycin, and kanamycin, which is especially preferred.

Recombinant gene expression depends upon transcription of the appropriate gene and efficient translation of the message. A failure to perform correctly either one of these processes can result in the failure of a given gene to be expressed. Transcription of a cloned insert requires the presence of a promoter recognized by the host RNA polymerase. Hence, in another embodiment of the invention, vectors are provided that incorporate promoter sequences for interaction with RNA polymerases to initiate transcription of cloned genes. In a preferred embodiment, the promoters interact with eukaryotic RNA polymerases. Such promoters include CMV immediate early, HSV thymidine kinase, early and late SV40, LTRs from retrovirus, and mouse metallothionein-I. CMV and Rous Sarcoma Virus long terminal repeat (RSV LTR) are preferred.

Efficient translation requires that the mRNA bear a ribosome binding site. In yet another embodiment of the invention, ribosome binding sites are introduced into the vectors so as to produce efficient translation of expressed transcripts. In eukaryotes, which do not put multiple cistrons under control of a single promoter and transcribe them as a single message, expression of polycistrons is a problem. For polycistronic plasmids, it is preferred, therefore, that the ribosome binding site be derived from encephalomyocarditis (EMC) virus. This site is incorporated into the vector where it can function as an internal entry point for initiation of translation by eukaryotic ribosomes.

Translational efficiency has been found to be regulated by specific sequence elements in the 5' non-coding or untranslated region (5' UTR) of the RNA. Positive sequence motifs include the translational initiation consensus sequence $(GCC)^A CCATGG$ (Kozak, Nucleic Acids Res. 15:8125 (1987)) and the 5' 7 methyl GpppG cap structure (Drummond et al., Nucleic Acids Res. 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, supra, Rao et al., Mol. and Cell. Biol. 8:284 (1988)). Vectors that feature positive sequence motifs facilitating translation and wherein negative elements have been eliminated are provided in another embodiment of the invention. Preferred, in this regard, is the Kozak consensus translation initiation sequence, especially the sequence "CACCATGG." Also preferred is the RSV LTR supra, wherein an inappropriate poly A addition sequence has been altered, to preclude a negative effect on gene expression.

In addition to transcription and translation concerns, mRNA stability must be considered. As a general statement, capping and 3' polyadenylation are the major positive determinants of mRNA stability (Drummond et al., Nucleic Acids Res. 13:7375 (1985); Ross, Mol. Biol. Med. 5:1(1988)) and function to protect the 5' and 3' ends, respectively, of the mRNA from degradation. Other regulatory elements which affect the stability of mRNAs have also been defined. The most notable and clearly defined of these are the uridine rich 3' untranslated region (3' UTR) destabilizer sequences found in many short half-life mRNAs (Shaw and Kamen, Cell 46:659 (1986)), although there is evidence that these are not the only sequence motifs which result in mRNA destabilization (Kabnick and Housman, Mol. and Cell. Biol. 8:3244 (1988)). Vectors designed to circumvent destabilization of mRNAs are provided in another embodiment of the invention, wherein, for example, they include 3' untranslated regions native to cloned genes. Vectors incorporating positive determinants of mRNA stability are also provided, which determininants preferably constitute poly A addition sequences. Polyadenylation sites derived from non-viral sources are preferred to avoid contamination with viral gene products; for example, bovine growth hormone gene derived poly A addition sequence is preferred. Also expressly contemplated and preferred are viral sources of poly A signals, such as SV40, where essentially all of any open reading frames encoding viral proteins contained therein have been deleted.

Gene expression may also be mediated by intron sequences. Such sites may underlie RNA processing in the nucleus and subsequent transport of mRNAs to the cytoplasm for translation. Such introns seem to function by facilitating splicing of expressed transcripts. According to another embodiment of the invention, vectors are optimized by inclusion of introns that facilitate splicing. A preferred intron is derived from SV40, wherein essentially all of any open reading frames have been deleted to obviate contamination with viral gene products. In this same regard, vectors may also be optimized by deletion of introns. In a preferred embodiment of the invention, the cDNA encoding HLA-B7 is rid of a native intron resulting in enhanced gene expression.

The optimized vectors provided herein may operate as cassettes in which cistrons or polycistrons of interest are substituted for acting cistrons or polycistrons whose expression is no longer desired.

pHLA-B7/β-2 Microglobulin Plasmid

The pHLA-B7/β-2 m. plasmid expression vector is a covalently closed circular DNA macromolecule that may be biosynthesized in bacterial cells grown in a selection media requiring the expression of the kanamycin resistance protein.

In addition to the kanamycin resistance gene, the plasmid DNA encodes the heavy (human HLAB7) and light (β-2 microglobulin) proteins of a Class 1 Major Histocompatability Complex (MHC) antigen. The plasmid is designed to express these two proteins via a bi-cistronic mRNA in eukaryotic cells. Initiation of transcription of the mRNA is dependent on a Rous Sarcoma Virus promoter sequence derived from the 3' Long Terminal Repeat. Termination of transcription is dependent upon the polyadenylation signal sequence derived from the bovine growth hormone gene. Eukaryotic cell translation of the heavy chain is regulated by the 5' cap-dependent protein start site. Translation of the light chain is controlled by a Cap Independent Translational Enhancer (CITE) sequence derived from the Encephalomyocarditis Virus. Finally, replication of the plasmid in bacterial cells is controlled by the presence of a bacterial origin of replication. There are no other significant open reading frames nor any known oncogenic sequences.

The plasmid has been characterized by DNA sequence analysis (SEQ ID NO.1). It is 4965 bp in size, with a base composition of 2335 adenines, 2630 cytosines, 2630 guanines, and 2335 thymines. This results in a molecular weight of $3.298437 \times 10^6$ g.m.u.

The pHLA-B7/β-2 m. plasmid may be constructed using independent segments of DNA cloned into a high copy number bacterial plasmid DNA. The plasmid components function to facilitate high levels of replication in bacterial cells, express a dominate selectable resistance protein during bacterial cell culture, and, when introduced into eukaryotic cells, effect a high level of expression of the two Class I MHC component proteins, HLA-B7 and β-2 microglobulin.

The backbone plasmid DNA is derived from pBR322, a vector widely used in molecular biology laboratories and whose origin of replication was taken from the naturally occurring bacterial plasmid, ColE1 (Bolivar, R., et al., *Gene* 2, 95 (1977). This 952 bp fragment of pBR322 used in the plasmid represents the region from pBR322 base number 2244 (Acc 1 restriction endonuclease site; blunt ended) to base number 3193 (Bsp H1 restriction endonuclease site), using the unique Eco R1 restriction endonuclease site as pBR322 base 1. This backbone plasmid fragment is found between base number 4014 and 4965 of pHLA-B7/β-2 m. plasmid and comprises a bacterial origin of replication. It does not contain any open reading frames known to be expressed in either bacterial or animal cells.

Eukaryotic gene expression is regulated by the Avian Rous Sarcoma Virus (RSV) 3' Long Terminal Repeat (LTR) promoter sequence. This sequence was derived from the Schmidt-Ruppin strain of RSV (Swanstrom, R., et al., *Proc. Nat'l Acad. Sci. U.S.A.* 78, 124 (1981)) and was cloned by isolating DNA bounded by the Pvu II site at viral base number 8673 and the Bfa I site at viral base number 9146. The use of this promoter sequence to regulate the expression of heterologous genes in eukaryotic cells was described more than 10 years ago by Gorman, C., et al. (*Proc. Nat'l. Acad. Sci. U.S.A.* 79, 6777 (1982)). The RSV DNA fragment used in the construction of the pHLA-B7/β-2 m. plasmid was taken from the pRSVβ-globin (Gorman, C., et al., *Science* 221, 551 (1983)). Although this regulatory sequence is found in an avian retrovirus, this 3' LTR has been tested and shown to have no intrinsic oncogenic activity in either avian or mammalian cells (Westphal, C., et al., *Cold Spring Harbor Symp. Quant. Biol.* 50, 411 (1985); Mahon, M., et al., *Proc. Nat'l. Acad. Sci. U.S.A.* 85, 1165 (1988); Overbeek, U., et al., *Science* 231, 1574 (1986)). The RSV LTR promoter domain in pHLA-B7/β-2 m. plasmid represents base pairs 1 through 529. This includes a 56 base pair region of chemically synthesized oligonucleotide DNA which modifies this regulatory sequence to effect a higher level of eukaryotic cell expression of the down stream coding sequences. The oligonucleotide removes a polyadenylation signal sequence (i.e. AATAAA with TCTAGA, an Xba I restriction endonuclease site) originally found in the RSV DNA sequence. It also introduces a strong translational signal sequence (Kozak, M., et al.) proximal to the translational initiating codon, $A^{535}TG$. Moreover, this synthetic oligonucleotide was also used to incorporate a number of restriction endonuclease sites (i.e., Sal I, Hind III, and Nco I) to facilitate subcloning of both 5' and 3' DNA elements.

The coding sequences for human HLA-B7 and β-2 microglobulin proteins are located 3' to the RSV LTR described above. While the two genes for these proteins are located at separate locations within the human genome, the expression of the genes and assembly of the two proteins appears to be interdependent. Therefore, in order to foster a high level of expression and assembly of the correct surface HLA antigen in a heterologous expression system, the two cDNA sequences have been cloned proximal to each other and 3' to the RSV promoter. Transcription of both sequences occurs via a single, bi-cistronic mRNA molecule is initiated by the RSV promoter domain and terminated by the distal bovine growth hormone transcriptional terminator/polyadenylation signal sequence. Translation of this bi-cistronic mRNA is affected by both CAP dependent (for HLA-B7) and CAP independent (β-2 microglobulin) ribosome recognition sequences. The CAP independent signal is taken from the murine encephalomyocarditis (EMC) virus genome and is cloned between the HLA-B7 heavy and light chains coding sequences and as part of the bicistronic mRNA.

The HLA-B7 cDNA sequence was isolated from a human B lymphocyte cDNA library and is close to the sequence found in GENBANK (HUMMHB7A). Moreover, it has been shown to induce an immune response characteristic of a foreign class I major histocompatibility complex antigen (Nabel, E., et al., *Proc. Nat'l Acad. Sci. U.S.A.* 89, 5157 (1992)). The cDNA sequence begins with the $A^{535}TG$ (within an Nco I restriction endonuclease site) and ends at base number 1853. The open reading frame from (i.e. $A^{535}TG$ to $T^{1621}GA$) within this sequence encodes a protein with a predicted molecular weight of 44,200. The remaining 230 base pairs represent a portion of the 3' untranslated mRNA sequence.

The sequence from base pair 1854 to 1888 is a portion of a multiple cloning site originally derived from a synthetic oligonucleotide. It forms a junction between the HLA-B7 sequence and the murine encephalomyocarditis CAP-Independent Translational Enhancer (EMCV-CITE) sequence and has been used to facilitate subcloning of both upstream and downstream sequences.

The 588 bp EMCV-CITE sequence is taken from a portion of the 5' region (255 to 843) of cloned EMCV genomic DNA (Duke, G., et al., *J. Virology* 66, 1602 (1992)). It is a non-coding regulatory sequence which functions as an internal entry point for the eukaryotic ribosomal subunits when located within a mRNA molecule. Therefore, it enables the translational start codon ($A^{2480}TG$) of β-2 microglobulin, downstream of the HLA-B7 stop codon on this biscistronic mRNA, to be recognized by the ribosome (Parks, G., et al., *J. Virology* 60, 376 (1986)).

The partial cDNA sequence for the human β-2 microglobulin (the light chain of the class I MHC heteroduplex surface antigen) was originally published by Suggs, S. et al., *Proc. Nat'l Acad. Sci U.S.A.* 78, 6613 (1981). Subsequent work by Alejandro Madrigal (Stanford University Medical School, Palo Alto, Calif.) has shown that the chimpanzee β-2 microglobulin cDNA differs by only 4 bases from the human sequence and encodes an homologous β-2 microglobulin protein. Consequently the chimpanzee cDNA was used in the DNA construct. The β-2 microglobulin open reading frame begins, as stated above, at $A^{2480}TG$ and ends at $T^{2837}AA$. 10 bases of the chimpanzee 3' untranslated domain remain downstream of this open reading frame prior to splicing of the sequence to a heterologous 3' untranslated, transcriptional termination and polyadenylation signal sequences derived from the bovine growth hormone gene. Splicing at this junction is carried out using a synthetic oligonucleotide (pHLA-B7/β-2 m. plasmid base pairs 2847 to 2870) recognized by both Hind III and Bam HI restriction endonucleases.

Base pairs 2871 to 3111 are derived from the bovine growth hormone (bgh) gene (Gordon, et al., *Mol. Cell. Endocrinology* 33, 81 (1983)). It begins at a blunt-ended Bgl II site within the 3' untranslated region of the mRNA coding sequence and extends to a point approximately 110–115 bases beyond the point of transcriptional termination and polyadenylation. There is a polyadenylation signal sequence ($A^{2979}ATAAA$) located within this domain. The 39 base pairs located between 3112 to 3151 represent a synthetic oligonucleotide fragment to facilitate cloning.

The final domain of pHLA-B7/β-2 m. plasmid comprises the bacterially expressed kanamycin resistance (kanamycin$^r$) gene sequence. The gene is taken from the transposable element Tn903 which has been fully characterized (Oka, A., et al., *J. Mol. Biol.* 147, 217 (1981)) and shown to confer drug resistance through the expression of a 30,7000 M.W. aminoglycoside 3'-phosphotransferase protein (Berg, D. et al., (1978) In Microbiolgy-1978 (Schlessinger, D. ed.] pp 13–15 American Society, for Microbiology, Washington, D.C.). The kanamycin$^r$ coding sequence is located on the strand opposite to that encoding the eukaryotic HLA-B7 and β-2 microglobulin sequences and is therefore read in the opposite direction from the eukaryotic genes. The open reading frame for kanamycin$^r$ begins at $A^{3967}TG$ and ends at $T^{3154}AA$. This sequence was cloned from a plasmid PET9a, a commercially available plasmid from Novagen, Inc. (Madison, Wis.).

Cationic Liposomes and Vehicles for Gene Delivery

The transfer of the optimized vectors provided herein into cells or tissues of organisms may be accomplished by injecting naked DNA or facilitated by using vehicles, such as, for example, viral vectors, ligand-DNA conjugates, adenovirus-ligand-DNA conjugates, calcium phosphate, and liposomes. Transfer procedures are art-known, such as, for example, transfection methods using liposomes and infection protocols using viral vectors, including retrovirus vectors, adenovirus vectors, adeno-associated virus vectors, herpes virus vectors, vaccinia virus vectors, polio virus vectors, and sindbis and other RNA virus vectors.

According to one embodiment of the invention, the vectors provided herein are complexed with cationic liposomes or lipid vesicles. Cationic or positively charged liposomes are formulations of cationic lipids (CLs) in combination with other lipids. The formulations may be prepared from a mixture of positively charged lipids, negatively charged lipids, neutral lipids and cholesterol or a similar sterol. The positively charged lipid can be one of the cationic lipids, such as DMRIE, described in U.S. application Ser. No. 07/686,746, which is hereby incorporated by reference, or one of the cationic lipids DOTMA, DOTAP, or analogues thereof, or a combination of these. DMRIE is 1,2-dimyristyloxypropyl-3-dimethylhydroxyethyl ammonium bromide (see, e.g., J. Felgner, et al., *J. Biol. Chem.*, 269, 1 (1994)) and is preferred.

Neutral and negatively charged lipids can be any of the natural or synthetic phospholipids or mono-, di-, or triacylglycerols. The natural phospholipids may be derived from animal and plant sources, such as phosphatidylcholine, phosphatidylethanolamine, sphingomyelin, phosphatidylserine, or phosphatidylinositol. Synthetic phospholipids may be those having identical fatty acid groups, including, but not limited to, dimyristoylphosphatidylcholine, dioleoylphosphatidylcholine, dipalmitoylphosphatidylcholine, distearoylphosphatidylcholine and the corresponding synthetic phosphatidylethanolamines and phosphatidylglycerols. The neutral lipid can be phosphatidylcholine, cardiolipin, phosphatidylethanolamine, mono-, di- or triacylglycerols, or analogues thereof, such as dioleoylphosphatidylethanolamine (DOPE), which is preferred. The negatively charged lipid can be phosphatidylglycerol, phosphatidic acid or a similar phospholipid analog. Other additives such as cholesterol, glycolipids, fatty acids, sphingolipids, prostaglandins, gangliosides, neobee, niosomes, oranyothernatural or synthetic amphophiles can also be used in liposome formulations, as is conventionally known for the preparation of liposomes.

Substitution of the cationic lipid component of liposomes can alter transfection efficiencies. Specifically, modification of the cationic species appears to be an important determinant in this process. A new formulation of cationic lipids is preferred in which a different cationic lipid, 1,2-dimyristyloxypropyyl-3-dimethylhydroxyetheyl ammonium bromide (DMRIE), is utilized with dioleoyl phosphatidylethanolamine (DOPE). This formulation has two properties which make it more suitable for transfections. First, it shows up to ~7-fold increase in improved transfection efficiency compared to the formulation DC-cholesterol/DOPE in vitro. See Example 6.

Importantly, this DMRIE/DOPE formulation does not aggregate at high concentrations, in contrast to the DC-Chol liposome. This characteristic thus allows higher absolute concentrations of DNA and liposomes to be introduced into experimental animals without toxicity. See Example 7. Because of these properties, it now becomes possible to introduce 100–1000 times more DNA which could markedly improve gene expression in vivo. See Example 8.

A preferred molar ratio of DMRIE to DOPE is from about 9/1 to 1/9; a molar ratio of about 5/5 is particularly preferred.

Using conventional cationic lipid technology and methods, the lipid compositions can be used to facilitate the intracellular delivery of genetic material coding for therapeutically or immunogenically active peptides. Briefly, such methods include the steps of preparing lipid vesicles composed of cationic lipids and using these lipid vesicles to mediate the transfection or transport of therapeutically or immunogenically active agents into the cells. The intracellular transport may be accomplished by incorporating or encapsulating the agent in the lipid vesicle and contacting the cell with the lipid vesicles, as in conventional liposome methodology; or alternatively, by contacting the cells simultaneously with empty lipid vesicles, comprising the cationic lipid formulations together with the agent, according to conventional transfection methodology. In the process of either strategy, the agent is taken up by the cell. The contacting step may occur in vitro or in vivo.

Such methods may be applied in the treatment of a disorder in an organism, comprising the step of administering a preparation comprising a cationic lipid formulation together with a pharmaceutically effective amount of a therapeutically active agent specific for the treatment of the disorder in the organism and permitting the agent to be incorporated into a cell, whereby the disorder is effectively treated. The agent may be delivered to the cells of the organism in vitro or in vivo. The in vitro delivery of an agent is carried out on cells that have been removed from an organism. The cells are returned to the body of the organism whereby the organism is treated. In contrast, in vivo delivery involves direct transduction of cells within the body of the organism to effect treatment. Cationic lipid mediated delivery of vectors encoding therapeutic agents can thus provide therapy for genetic disease by supplying deficient or missing gene products to treat any disease in which the defective gene or its product has been identified, such as Duchenne's dystrophy (Kunkel, L. and Hoffman, E. *Brit. Med. Bull.* 45(3):630–643 (1989)) and cystic fibrosis (Goodfellow, P. *Nature*, 341(6238):102–3 (Sep. 14, 1989)).

The cationic lipid mediated intracellular delivery described can also provide immunizing peptides. The above transfection procedures may be applied by direct injection of cationic lipid formulations together with a vector coding for an immunogen into cells of an animal in vivo or transfection of cells of an animal in vitro with subsequent reintroduction of the transduced cells into the animal. The ability to transfect cells with cationic lipids thus provides an alternate method for immunization. The gene for an antigen is introduced, by means of cationic lipid-mediated delivery, into cells of an animal. The transfected cells, expressing the antigen, are reinjected into the animal or already reside within the animal, where the immune system can respond to the antigen. The process can be enhanced by co-administration of either an adjuvant or cytokines such as lymphokines, or a gene coding for such adjuvants or cytokines or lymphokines, to further stimulate the lymphoid cells and other cells mediating the immune response.

Administration to patients diagnosed with neoplastic disease of DNA liposome complexes for the treatment of neoplasia involves, preferably, intratumoral injection, by needle and syringe or by catheter (see infra), of the complexes. Plasmid DNA in an amount ranging from about 0.1 microgram to about 5 g is administered in from about 0.15 nanoMolar to about 1.5 milliMolar liposome solution. In a preferred protocol, 0.1 ml of plasmid DNA (0.05–50 mg/ml) in lactated Ringer's solution is added to 0.1 ml of DMRIE/DOPE liposome solution (0.15–15 microMolar), and 0.8 ml of lactated Ringer's solution is added to the liposome DNA solution. In this preferred protocol, three aliquots of 0.2 ml each are injected into a nodule or one aliquot of 0.6 ml is applied by catheter. The patient, in this preferred protocol, is thus administered a dose ranging from about 3 microgram to about 3 milligram of DNA and from about 4.5 nanoMolar to about 4.5 microMolar DMRIE/DOPE. Doses are repeated at two-week intervals.

Optimal transfection parameters relating to such aspects as toxicity and composition may be identified by comparing the effectiveness of DNA/cationic lipid formulations in transfecting cells using the 96-well microtiter plate assay which is set forth in Example 12 and has been described in detail elsewhere (e.g., Feigner, J. H. and Felgner P. L., "Lipofection," *Protocols in Cell & Tissue Culture*, 1993, John Wiley & Sons) and may be confirmed in experimental animals prior to administration to patients. See, also, Example 14.

Catheter Based Gene Therapy

In a preferred embodiment of the invention, direct gene transfer into target cells, such as tumor cells, in situ is employed as a method to optimize the delivery of genes in vivo. Traditionally, gene transfertechniqueshave focusedon-modification of target cells in vitro, followed by transfer of modified cells. Such approaches subject these cells to selection and different growth conditions from those which act in vivo. Because they also require that cell lines be established for each application, adaptability to human disease is more difficult and requires more time.

It is preferred to deliver recombinant genes through direct intracellular injection and, more preferably, by the use of a catheter. Catheters have been used to introduce recombinant genes in vivo (see, e.g., E. G. Nabel, et al., *Proc. Natl. Acad. Sci. USA* 89, 5157 (1992); E.G. Nabel, et al., *Science* 249, 1285 (1990); E. G. Nabel, et al., *Science* 244, 1342 (1989); E. G. Nabel, et al., *J. Clin. Invest.* 91, 1822 (1993); G. Plautz, et al., *Circ.* 83, 578 (1991); E. Nabel, et al., *Nature* 362, 844 (1993)). A catheter was utilized in a human clinical trial for one patient with a pulmonary metastases in a protocol directed to the treatment of melanoma disease using gene therapy. Treatment by catheter was well-tolerated by the patient. No complications or toxicities were noted (see Example 13). Compared to intratumoral injection, this invention provides the ability to transduce a larger percentage of cells within the tumor microcirculation in order to achieve greater efficacy of gene expression, at the same time minimizing the potential for inadvertent microscopic seeding of tumor cells to distant sites.

In the aforementioned patient, the gene was delivered through the pulmonary artery which does not directly perfuse the tumor with oxygenated blood. One may, alternatively, introduce the gene through feeding arteries. For example, the hepatic artery may be used to deliver DNA liposome complexes to either primary or secondary tumors metastatic to the liver.

Because this approach employs direct gene transfer in vivo, it can be applied easily in a clinical setting to spontaneously arising tumors, alone or in combination with cytokines or other adjuvant treatments, including adoptive lymphocyte transfer, to augment tumor immunity.

Expression in Different Tumor Cell Types In vivo

It was previously shown that the HLA-B7 gene can be expressed in a few different tumor cells in vivo (G. E. Plautz, et al., *Proc. Natl. Acad. Sci. USA* 90, 4645 (1993)). Our data suggests that successful expression of HLA-B7 and $\beta$-2 microglobulin gene can be obtained in human melanoma (see Example 4). Thus, according to an embodiment of the invention, treatment of human melanoma disease is provided. Also provided are treatments of other human cancers, for example, colon carcinoma, renal cell carcinoma, breast adenocarcinoma, hepatoma, lung carcinoma and pancreatic carcinoma.

Particular aspects of the invention may be more readily understood by reference to the following examples, which are intended to exemplify the invention, without limiting its scope to the particular exemplified embodiments.

EXAMPLE 1

Preparation of HLA-B7 & $\beta$-2 Microglobulin Containing Plasmid

A vector for the expression of HLA-B7 and $\beta$-2 microglobulin was constructed by a series of steps. The starting construct was the plasmid RSV $\beta$-globin (C. Gorman, et al., *Science* 221, 551 (1983) and C. Gorman, et al., *Mol. Cell. Biol.* 2, 1044 (1982)) in which the HLA-B7 gene cDNA was to be inserted. The RSV $\beta$-globin plasmid was composed of the ampicillin-resistance cistron and the origin of replication from plasmid pBR322 joined to a hybrid eukaryotic transcription unit. The transcription unit in this plasmid was constructed of the RSV LTR promoter, rabbit $\beta$-globin coding sequence, and SV40 mRNA processing signals, including the small-t intron and early region polyadenylation site. The $\beta$-globin gene was removed from the plasmid by digestion with Hind III and Bgl II. After treatment with calf intestinal phosphatase (CIP) and Klenow fragment of DNA polymerase, the backbone was used to insert a Bam HI to Sal I fragment of HLA-B7 treated with Klenow enzyme. The fragment had been obtained from the pLJ HLA-B7 vector (E. G. Nabel, et al., *Proc. Natl. Acad. Sci. USA* 89, 5157 (1992)).

The resultant RSV HLA-B7 plasmid was improved by the removal of an intron in the HLA-B7 coding sequence. Removal of the intron resulted in higher expression levels in transient transfection assays of cultured cells. Site directed mutagenesis was accomplished by way of the oligonucleotide-directed gap heteroduplex technique (G. Nabel, D. Baltimore, *Nature* 326: 711 (1987)). Oligonucleotides having the sequence 5'-CCG AGA CCT GGG CCG GCT CCC (bases 593–613 of SEQ ID NO.1) and ACT CCA TGA G-3' were employed. The plasmid RSV HLA-B7 (intron-less) was further modified as follows.

A "Kozak" consensus translation initiation sequence (Kozak, *Nucleic Acids Res.* 15: 8125 (1987)) was added to increase translation efficiency of the HLA-B7 message. Again, the oligonucleotide-directed gap heteroduplex technique was utilized. The Kozak sequence "CACC" was inserted 5' to the initiation codon by the use of oligonucleotides having the sequence 5'-CAC CTC CAA GCT T CA CCA TGG (bases 518–538 of SEQ ID NO.1) and TGG TCA TGG CGC-3' (bases 539–550 of SEQ ID NO.1). The product was called RSV HLA-B7(K).

In order to make the vector bicistronic, so that β-2 microglobulin peptide would be expressed in addition to HLA-B7 antigen, it was necessary to include an internal ribosome initiation site to permit translation of the second message. Towards this end, a fragment containing such a site derived from encephalomyocarditis (EMC) virus was removed from pCITE-1, procured from Novagen (Madison, Wis.), by digestion with Eco RI and Xba I. The fragment was ligated into pBluescript SK, a cloning vector purchased from Stratagene (La Jolla, Calif.), which had been digested with Eco RI and Xba I. The internal ribosome initiation site-containing plasmid, rendered advantageous by the presence of multiple cloning sites, was named pBS CITE I.

A plasmid that featured a β-2 microglobulin gene was constructed as follows. The β-2 microglobulin gene was obtained as a Sal I/Bam HI fragment treated with Klenow from pHβ Apr-1-Neo, provided by Dr. Madrigal of Stanford University. The fragment was joined upstream of a poly-adenylation addition signal derived from bovine growth hormone gene by ligation into a plasmid containing such a signal. The plasmid, PRSV ADH, supplied by Dr. Culp of Case western Reserve University, was digested with Hind III and Xba I to remove the gene encoding ADH contained therein and treated with CIP and Klenow before insertion of the β-2 microglobulin gene containing fragment. Using site directed mutagenesis, the resultant plasmid was improved by the addition of a Kozak sequence (CACC) to enhance translation efficiency of the β-2 microglobulin transcript. The oligonucleotides employed to direct the gapped heteroduplex consisted of the sequences 5'-CAC CTC CAA GCT TCA CCA TGG CTC and GCT CCG TGG-3' (A CCA TGG CTC GCT CCG TGG correspond to bases 2477–2495 of SEQ ID NO. 1). Thus, a plasmid was available, termed pRSVβ2(K), that included the β-2 microglobulin gene positioned between a Kozak sequence and the bovine growth hormone gene derived polyadenylation signal.

Consequently, the multiple cloning sites in pBS CITE I were exploited to place the β-2 microglobulin gene downstream of the internal ribosome initiation site. This was accomplished by implementing pBS CITE I as a backbone in which a Nco I/Xba I fragment was removed, first, by digestion with Xba I and treatment with Klenow, and, second, by digestion with Nco I. The β-2 microglobulin gene, replete with Kozak sequence and poly A signal, was acquired as a fragment by digesting pRSVβ2(K) with Dra III and filling in with Klenow and subsequently digesting with Nco I. Ligation produced a plasmid containing a unit composed of an internal ribosome initiation site followed by the β-2 microglobulin gene and a polyadenylation signal.

This unit was inserted into RSV HLA-B7(K) supra as follows. The HLA-B7 containing plasmid was partially digested by Bgl II sufficient to cut at that Bgl II site 3' of the HLA-B7 encoding sequence rather than at that Bgl II site internal to the HLA-B7 gene. RSV HLA-B7(K) was thus linearized, treated with CIP, and filled in with Klenow. The β-2 microglobulin comprising unit was removed as a Sal I/Not I fragment that was subsequently treated with Klenow. The ligation product contained a bi-cistronic transcription unit incorporating the RSV promoter followed by (in the direction of transcription): the HLA-B7 gene (attached to a Kozak sequence), an internal ribosome initiation site, the β-2 microglobulin gene (also attached to a Kozak sequence), the bovine growth hormone gene derived poly A site, and SV40 processing sequence. It was desired to remove the SV40 sequence in order to reduce contamination with virally derived genetic material, but not until the ampicillin resistance cistron was deleted and the kanamycin resistance gene inserted.

In order to facilitate purification of the plasmid, and to obviate the use of ampicillin selection during the growth of the bacterial host, the gene encoding ampicillin resistance (b-lactamase) was replaced with the gene encoding kanamycin resistance (aminoglycoside phosphotransferase) from the bacterial transposon Tn903. First, an Alw NI partial/Eco RI digest of RSV HLA-B7(K) supra was ligated with an Alw NI/Eco RI fragment from the vector pET9a (Novagen, Madison, Wis.) that encoded kanamycin resistance. Second, the resultant construct, named kRSV HLA-B7(K), was used as a donor of a Nde I/Hpa I kanamycin resistance gene containing-fragment. This fragment was substituted for an Nde I/Hpa I fragment that coded for ampicillin resistance subsisting within the plasmid of interest. The exchange of the antibiotic resistance genes having been completed, the removal of the unwanted SV40 sequence was addressed.

The SV40 processing and polyadenylation sequence was eliminated as a Xho I/Eco RI fragment. By partial digestion of the plasmid with Xho I and Eco RI, cutting was avoided in the kanamycin resistance cistron at an internal Xho I site and at three Eco RI sites in the bi-cistronic transcription unit. Subsequent treatment with Klenow and ligation produced a construct desirable in all aspects except one.

Within the RSV LTR was encrypted a polyadenylation signal, "AATAAA," that was inappropriate by virtue of its location within sequence intended to function as a promoter. Using site directed mutagenesis, the poly A sequence was mutated. The oligonucleotides having the sequence 5'-CTA GCT CGA TAC TCT AGA CGC (bases 470–490 of SEQ ID NO.1) and CAT TTG ACC-3' effectively directed the gapped heteroduplex, resulting in mutation of the unwanted poly A signal and, additionally, creation of a Xba I restriction site. A plasmid encoding HLA-B7 antigen and β-2 microglobulin peptide was thus prepared featuring many advantageous characteristics.

For example, the construct contained an origin of replication derived from pBR322, a bi-cistronic transcription unit under the control of a single promoter, a promoter derived from Rous sarcoma virus long terminal repeat (RSV-LTR) in which a poly A site had been mutated, an internal ribosome initiation site, consensus translation initiation sequences upstream of the HLA-B7 cistron (from which an intron had been removed) and the β-2 microglobulin cistron, a polyadenylation addition signal derived from bovine growth hormone gene, and genetic material encoding kanamycin resistance. Although it is preferred that the recombinant plasmid encode HLA-B7 and β-2 microglobulin, either cistron within the bi-cistronic transcription unit may be removed and the backbone used as a cassette for the insertion of other cistrons for which it is desired to achieve expression.

Database searching of the nucleotide sequence of the described plasmid through Genbank revealed no homology to oncogenes in the predicted open reading frames. Additionally, several papers have shown that the RSV+ pBR322 sequences used in this plasmid have been used successfully in transgenic mice and are not intrinsically oncogenic (Westphal et al., *Cold Spring Harb. Symp. Quant Biol.* 50:411–416, 1985; Mahon et al., *Proc. Natl. Acad. Sci. USA* 85:1165–1168, 1988; Overbeek et al., *Science* 231:1574–1577, 1986). Moreover, the plasmid described here was analyzed in a rat fibroblast transformation assay and did not stimulate an increase in colony transformation above background.

EXAMPLE 2

Preparation of HLA-B7 Containing Plasmid

This plasmid was prepared by beginning with plasmid kRSV HLA-B7(K) supra. The kRSV HLA-B7(K) construct contained a transcription unit including the RSV LTR as the promoter for a cDNA encoding the gene for HLA-B7 from which an intron had been removed. A Kozak consensus translation initiation sequence was present. The transcription unit also included regions derived from SV40 which allowed splicing at the 3' end of the cDNA, and a polyadenylation signal. Additionally, the vector contained the origin of replication derived from pBR322. Moreover, the recombinant molecule accommodated the dominant selectable marker for kanamycin resistance.

An overall reduction of SV40 sequences, from 1612 bp to 384 bp, was engineered. Deletions removed two open reading frames encoding portions of SV40 viral proteins, the small t antigen and VPI.

The polyadenylation region was originally cloned as a 993 base pair fragment from a Bcl I to Eco RI site from the SV40 viral genome. Extraneous sequences in this region coded for a viral structural protein, VPI. Elimination of extraneous regions of the SV40 polyadenylation signal was accomplished by deleting a 757 bp fragment from Eco RI to Bam HI from kRSV HLA-B7(K), leaving a 236 bp sequence containing the polyadenylation site.

The SV40 small t antigen intron was originally cloned as a 610 bp fragment, although the intron region itself was 64 bp in size. A 462 bp portion was deleted from the Pfl MI to Bsa BI site of kRSV HLA-B7(K), leaving a 148 bp region containing the intron. This deletion removed essentially all of the small t antigen open reading frame.

Thus, an HLA-B7 antigen encoding plasmid was developed to incorporate many advantageous features. For instance, by changing the drug resistance marker from ampicillin to kanamycin, patients who are exposed to the plasmid, e.g., during gene therapy, are protected from suffering antibiotic-related allergic reactions. What is more, ampicillin tends to decompose in culture, so the plasmid is inclined to be lost during in vitro growth; this problem is precluded by the use of a kanamycin selectable marker. Importantly, the eradication of two open reading frames encoding portions of SV40 viral proteins lowers the risk of tumorigenicity. The vector may also operate as a cassette into which cistrons may be inserted and removed at will for the transcription and subsequent translation of peptides of interest.

Database searching of the nucleotide sequence of the described plasmid through Genbank revealed no homology to oncogenes in the predicted open reading frames. In addition, the plasmid described here was analyzed in a rat fibroblast transformation assay and did not stimulate an increase in colony transformation above background.

EXAMPLE 3

EXPRESSION USING MODIFIED HLA-B7 EXPRESSION VECTOR

FACS analysis of plasmid HLA-B7 expression vector with no modifications or with an intron removed and the addition of a β-globin consensus translational initiation sequence revealed an increase in expression with these two modifications.

EXAMPLE 4

EXPRESSION USING HLA-B7 AND β-2 MICROGLOB. EXPRESSION VECTOR

Class MHC I proteins are co-transported with β-2 microglobulin to the cell surfaces. In 10% of melanomas, β-2 microglobulin and this class I MHC expression is lacking. To overcome this potential block to class I MHC expression, we included β-2 microglobulin in the vector. Expression of HLA-B7 with or without β-2 microglobulin gene in a β-2 microglobulin negative human melanoma line was evaluated. FACS analysis indicated that inclusion of the β-2 microglobulin gene allowed the expression of the HLA-B7 protein on the surface of cells which was otherwise not expressed.

EXAMPLE 5

IMPROVED THERAPY USING CYTOKINE GENES

The introduction of a class I MHC gene into tumors in vivo leads to T cell response against the foreign MHC gene, which also leads to recognition of tumor-associated antigens. The antigenicity of the tumor could be further augmented by the inclusion of cytokines which could further expand the T cells which are generated locally in response to this foreign gene. To determine whether this response can be further amplified, one might evaluate other cytokine genes, for example, IL-2, in combination with HLA-B7 in intratumor injections. In addition, one might also examine the response to is foreign MHC gene expression in the model using porcine arteries in vivo (E. G. Nabel, et al., *Proc. Natl. Acad. Sci. USA* 89, 5157 (1992)).

EXAMPLE 6

TRANSFECTION EFFICIENCY OF DMRIE/ DOPE

Cationic lipid formulations comprising DC-Cholesterol/ DOPE (5:5 molar ratio) and DMRIE/DOPE (5:5 molar ratio) were used to transfect cells according to the procedure of Example 12. Transfection efficiencies in vitro of the DC-Cholesterol/DOPE versus the DMRIE/DOPE cationic lipids were measured using β-galactosidase transduction of a renal epithelial cell (293), human melanoma line (HALL) or a murine fibrosarcoma (MCA 205). Compared to DC-cholesterol/DOPE, DMRIE/DOPE showed up to ~7-fold increase in transfection efficiency.

EXAMPLE 7

TOXICITY OF DNA LIPOSOME COMPLEXES

The potential toxicity of DNA liposome complexes was evaluated in animals injected with DNA liposome complexes (plasmid HLA-B7 infra+DMRIE/DOPE) by tail vein in concentrations that would exceed the amounts used in human trial by ~100-fold. There were no significant changes which would suggest major organ toxicity. To address the concern regarding potential cardiac toxicity, CPK levels were analyzed, and no changes were noted after injection. Electrocardiographic analysis revealed no myocardial toxicity. Serum biochemical parameters were within normal limits after single (1) or multiple injections (3× at 2-week intervals). There were no changes in BUN, creatinine, SGOT, SGPT, alkaline phosphatase, or bilirubin. Amylase, phosphorous, and total protein also remained stable following these treatments, both acutely and chronically. Finally, general safety tests revealed no loss in weight or signs of systemic toxicity after use of these DNA liposome complexes.

EXAMPLE 8

IMPROVED THERAPY WITH DNA DMRIE/DOPE COMPLEXES

The potential for improved therapy with the new liposome formulation DMRIE/DOPE was examined. C57/BL6 mice (H-2$K^b$) were inoculated subcutaneously in the left posterior hind flank on day 0 with tumor cells derived from a subclone of MCA 205, a murine fibrosarcoma (H-2$K^b$). Presensitization was performed by subcutaneous injection of BALB/c (H-2$K^d$) spleen cells (5×10$^6$) on day −6, and (2×10$^6$) on day +1. Tumors were injected with 0.1 ml of a 50:50 mixture of DMRIE:DOPE, containing 74.7 nmol DMRIE in lactated Ringer's solution, complexed with 5 μg of CMVH-2$K^b$, or CMVH-2$K^d$, on days 15, 18, and 20. Tumor size, calculated as the product of two perpendicular diameters, was measured on days 15, 18, 21, 23, 25, 28 and 30. Results indicated that the murine fibrosarcoma was poorly transfected by DC-Chol liposome using the concentration of the DMRIE/DOPE formulation. A marked anti-tumor effect was obtained after introduction of a foreign MHC gene (H-2$K^d$) which was not seen with DC-Chol.

EXAMPLE 9

PREPARATION OF 1,2-DIMYRISTYLOXYPROPYL-3-DIMETHYL-HYDROXYETHYL AMMONIUM BROMIDE (DMRIE)

DMRIE was synthesized using minor modifications of the procedure developed for the synthesis of DOTMA (Felgner, P. L. et al., PNAS 84: 7413–7417 (1987)). Thus, 3-dimethylamino-1,2-propanediol was condensed with myristyl mesylate employing basic catalysis to generate the corresponding diether. Subsequent to chromatographic purification of this lipophilic amine, quatranization was effected by treatment with 2-bromoethanol at elevated temperatures. The chromatographically purified product exhibited IR, $^1$H-NMR and elemental analyses consistent with those predicted for the desired hydroxyalkyl ammonium salt.

EXAMPLE 10

CATIONIC LIPOSOME PREPARATION

Cationic liposomes were prepared by mixing a chloroform solution of the lipid in a Wheaton 2 ml glass septum vial and removing the chloroform by rotary evaporation to produce the dried lipid film. Vials were placed under vacuum overnight to remove the solvent traces. One ml of deionized water was added, and the vials were sealed and vortexed for 1 minute at room temperature to produce large multilamellar vesicles (MSV). Small sonicated unilamellar vesicles (SUV) were prepared by sonicating the MLV under nitrogen in an inverted cup sonicator (Heat systems) for 60 minutes at 10 degrees C.

EXAMPLE 11

POLYNUCLEOTIDE/CATIONIC LIPID COMPLEX FORMATION

Polynucleotide complexes were prepared by mixing 0.5 ml of a 10 μg/ml polynucleotide solution with 0.5 ml of liposomes at 40–100 μg/ml. The diluted polynucleotide and liposome solutions were prepared from concentrated stock solutions by dilutions performed at room temperature. This procedure results in positively charged complexes which will spontaneously deliver polynucleotide into cells. Different ratios of positively charged liposomes to polynucleotides can be used to suit the need. These methods are essentially as described in Felgner, P. L. et al., PNAS 84: 7413–7417 (1987), and Felgner, P. and M. Holm, Focus 11(2) Spring, 1989. See, also, Example 14.

EXAMPLE 12

TRANSFECTIONS PROTOCOLS

Transfections were carried out in 96-well plates, as follows:

(1) The wells of a 96-well microtiter plate were seeded with 20,000 to 40,000 cells per well;

(2) Dilutions of cationic lipid preparations and polynucleotide preparations from stock solutions were carried out by 2-dimensional serial dilutions in two separate 96-well plates;

(3) Corresponding dilutions of lipid and polynucleotide were mixed by transferring an equal volume of polynucleotide to a corresponding lipid microwell;

(4) The serum-containing media was evaporated from the wells containing the cells;

(5) A quantity of about 100 μl of the cationic lipid/DNA complexes was added to cells in each well of the microtiter plate;

(6) The plates were incubated at 37° C. (5% $CO_2$). At 4–24 hours post transfection, an aliquot of 10% serum in Optimem™ Reduced Serum Media obtained from Gibco/BRL, (Gaithersburg, Md.) was added to each well;

(7) At the end of the incubation, the assay media of the cells or a whole cell lysate was assayed for expression activity.

Where beta-galactosidase was the reporter gene, the expression was monitored calorimetrically, using 2-nitrophenyl-β-D-galactopyranoside (ONPG) or chlorophenyl red-β-D-galactopyranoside (CPRG) as a substrate, reading the plates with a microtiter reader at 405 nm.

EXAMPLE 13

CATHETER BASED GENE DELIVERY

A catheter-based delivery introduction of a foreign MHC gene into a melanoma pulmonary metastasis was used in a patient who had previously received gene transfer treatment. This procedure was tolerated well with no change in arterial pressures before and after treatment (23/12 mean=10 versus 22/11 mean=10) following gene is transfer. In addition, no acute or chronic toxicity was noted after these treatments. Analysis of hematology, chemistry, and immunology assays revealed no additional abnormalities up to 6 weeks after the initial treatment.

EXAMPLE 14

HUMAN GENE THERAPY

Patients diagnosed with melanoma are admitted to a clinical research center. The tumor nodule to be injected is identified and its borders measured prior to injection. A needle biopsy is performed to confirm the diagnosis. Tissue is stored as frozen sections for further immunohistochemical analysis and PCR. In addition, this nodule and other control (untreated) nodules are imaged by CT immediately prior to the procedure, and the size quantitated. The skin overlying the tumor nodule is sterilized and anesthetized using 0.01% lidocaine. For gene transfer, a 22-gauge needle is used to inject the DNA liposome complex which is prepared as follows: 10 minutes prior to delivery, 0.1 ml of plasmid DNA (0.05–50 mg/ml) in lactated Ringer's solution is added to 0.1 ml of DMRIE/DOPE liposome solution (0.15–15 $\mu$M). Each component is stored separately in sterile vials and certified as acceptable by the FDA. The solution is left at room temperature for 5–10 minutes and 0.8 ml of sterile lactated-Ringer's is added to the liposome DNA solution. The optimal composition of the DNA/liposome complex has been established for each batch by titration of DNA concentration and liposome concentration independently on human melanoma or renal cell carcinoma in culture, and confirmed by direct injection into melanoma or other tumors in experimental animals prior to use. Each component, the liposome preparation and the DNA, is tested for contaminants and toxicity and used according to previously established guidelines from the FDA. The liposome solution and DNA are aliquoted in individual sterile vials mixed under sterile conditions.

The optimal dosage of plasmid may be readily determined using conventional empirical techniques. For example, to optimize dosage for direct injection of the HLA-B7 plasmids, escalating doses are studied. Four groups of patients are studied sequentially with at least 1 month of observation prior to evaluation of the next group. Patients in each group receive intratumor injections. Group I receives 3 injections of 0.2 ml within the same nodule (3 $\mu$g of DNA+4.5 nM DMRIE/DOPE). Group II receives the same treatment with a 10-fold higher concentration of DNA liposome complex. Group III receives a 100-fold higher dose, and Group IV receives a 1000× higher amount. Pretreatment with low dose cytoxan may improve the anti-tumor response by eliminating suppressive T cells.

For catheter-based gene delivery, the same dose escalation is used, except a single 0.6 ml injection into the end artery which perfuses an isolated nodule is used with an occlusion balloon catheter. In murine and porcine models, the highest treatment exceeded these proposed doses by 100-fold and are well-tolerated. Doses are repeated within each subject for whom the toxicity treatment is with ≦grade II. Dose escalation begins if patients show toxicities <grade III from the treatment. If one/third of patients displays toxicity >grade II, the treatment is repeated on additional patients. If more than one-third of patients develops toxicity >grade II, the dosage is reduced. The maximal tolerated dose is defined as the dose at which one/third or more of patients develop grade III or IV toxicity. The treatment dose is established at one level below the maximum tolerated dose. Once the treatment dose is defined, an additional number of patients is entered at that dose to ascertain the safety of this dose for wider application.

Prior to the injection with the needle in place, gentle aspiration is applied to the syringe to ensure that no material is injected intravenously. Immediately after the injection procedure, a blood sample is obtained to check serum enzymes, chemistries, and blood counts, and to analyze for the presence of plasmid DNA in the peripheral blood by PCR. The patient is observed in the clinical research center for an additional 48 hours. If there are no complications, the patient is discharged after 48 hours. Should any abnormalities appear, the patient is kept for further observation.

Confirmation of Gene Transfer and Expression

Needle biopsy of the injected nodule is performed after administration of local anesthesia prior to injection and subsequent to treatment. A portion of this tissue is processed to obtain DNA for PCR analysis. The remaining tissue is processed for pathologic analysis and immunohistochemical and/or immunofluorescent staining. If sufficient material can be obtained, RNA PCR analysis is also performed. For internal organs, CT or ultrasound guided thin needle biopsies is also obtained when possible.

Analysis of Immune Response

Evidence of gene transfer can also be obtained indirectly by examination of the specific immune response to HLA-B7. The analysis is performed as follows: two weeks prior to the initial treatment, a blood sample is obtained to derive lymphocytes which are immortalized using the Epstein-Barr virus. An aliquot of these cells are further infected with an amphotropic HLA-B7 retroviral vector, and expression is confirmed on the cell surface. These cells are subsequently used in the laboratory as target cells for the cytolytic T cell assay.

Repeated Treatment

If no adverse side effects of the treatment are observed, repeated injections are considered at two-week intervals. Doses identical to the initial treatment regimen are repeated with similar protocols and observation as described above.

Confirmation of Recombinant Gene Expression

Several independent techniques are used to evaluate the presence and expression of the recombinant gene in vivo. Monoclonal antibodies to HLA-B7 are used to detect the recombinant gene product in vivo by immunohistochemistry. Fluorescence staining of freshly dispersed cells is also evaluated. The presence of plasmid DNA is confirmed by PCR of DNA from tumor tissue, peripheral blood lymphocytes, or in autopsy specimen tissue. If sufficient tissue is available, RNA is isolated and examined for the presence of HLA-B7 mRNA by PCR or S1 nuclease analysis.

Analysis of Immune Response

Direct gene transfer and expression of the HLA-B7 gene may sensitize the patient to HLA-B7 and lead to the generation of an immune response to this antigen. Limiting dilution analysis (LDA) is utilized to evaluate alterations in the frequency of helper and cytolytic T cells for HLA-B7 in the peripheral blood following direct gene transfer. Peripheral blood lymphocytes (PBL) are isolated and cryopreserved prior to, and at 4-week intervals, following the initial direct gene transfer. At the completion of treatment, samples of PBL from each time point are simultaneously evaluated for responsiveness to HLA-B7 by culturing PBL, under LDA conditions, with autologous EBV-B cells transduced with the HLA-B7 gene. Antigen specific elaboration of IL-2 or generation of CTL to HLA-B7 positive target cells are the indices evaluated in these studies. The presence of antibody is evaluated by FACS analysis of a matched pair of HLA- B7+ or HLA-B7− cell lines. In some instances, lymphocytes are isolated directly from the tumor, expanded in tissue culture, and analyzed for cytolytic function. Tumor biopsies at 7–14 days after treatment are analyzed by immunohistochemistry. It may be attempted to expand draining lymph node T cells or TIL cells to test their cytologic function. It may be possible to derive autologous cell lines to be used as targets in $^{51}$Cr release assays. An attempt may be made to excise tumor tissue prior to treatment for diagnosis, immunohistochemistry, and cryopreservation and to evaluate delayed type hypersensitivity reactions to the tumor before and after treatment.

While particular embodiments of the invention have been described in detail, it will be apparent to those skilled in the art that these embodiments are exemplary rather than limiting, and the true scope of the invention is that defined within the following claims:

What is claimed is:

1. A polycistronic plasmid comprising a first cistron encoding a MHC class I chain and a second cistron encoding a β-2 microglobulin chain.

2. The plasmid of claim 1 wherein said cistrons are organized in a transcription unit under the control of a single promoter, and said plasmid further comprises an internal ribosome entry site positioned between said cistrons.

3. The plasmid of claim 2 wherein said promoter is a RSV LTR promoter.

4. The plasmid of claim 3 wherein said RSV LTR promoter contains no open reading frames and no polyadenylation signals.

5. The plasmid of claim 2 wherein said internal ribosome entry site is a EMCV internal ribosome entry site.

6. The plasmid of claim 2 wherein said cistrons lack introns of the genes encoding said chains.

7. The plasmid of claim 2 wherein said cistrons contain translation initiation consensus sequences operably linked to the genes encoding said chains.

8. The plasmid of claim 2 further comprising a bovine growth hormone gene transcription termination and polyadenylation signal sequence operably linked to said transcription unit.

9. The plasmid of claim 2 further comprising a selectable marker operably encoding a kanamycin resistance gene.

10. The plasmid of claim 2 further comprising a pBR322 sequence containing a prokaryotic origin of replication and lacking an open reading frame.

11. The plasmid of claim 2 wherein said MHC Class I chain is HLA-B7.

12. The plasmid of claim 1 further comprising:

(a) a transcription unit, wherein said cistrons are organized in said transcripion unit under the control of a single RSV LTR promoter, (b) an internal ribosome entry site positioned between said cistrons, (c) a bovine growth hormone gene transcription termination and polyadenylation signal sequence operably linked to said transcription unit, (d) a selectable marker operably encoding kanamycin resistance, and (e) a pBR322 sequence containing a prokaryotic origin of replication.

13. The plasmid of claim 1 having the DNA sequence set forth in SEQ ID NO:1.

14. A pharmaceutical composition comprising a therapeutically effective amount of the plasmid of claim 1 or 12, and a pharmaceutically acceptable carrier.

15. The pharmaceutical composition of claim 14 further comprising a transfer-facilitating vehicle.

16. The pharmaceutical composition of claim 15 wherein said vehicle comprises a transfection-facilitating cationic lipid formulation.

17. The pharmaceutical composition of claim 16 wherein said formulation is DMRIE-DOPE.

18. The pharmaceutical composition of claim 17 wherein said DMRIE-DOPE has a molar ratio of 5:5.

19. A method of suppressing solid tumor growth in a mammal comprising administering to said mammal the pharmaceutical composition of claim 14 at or around the site of a solid tumor wherein said solid tumor is suppressed growth.

20. The method of claim 19 wherein said administration is mediated by a catheter.

21. The method of claim 19 wherein said administration comprises direct intratumoral injection.

22. The method of claim 19 wherein said tumor is a melanoma.

* * * * *

UNITED STATES PATENT AND TRADEMARK OFFICE
CERTIFICATE OF CORRECTION

PATENT NO. : 5,910,488
DATED : June 8, 1999
INVENTOR(S) : Nabel et al.

It is certified that error appears in the above-identified patent and that said Letters Patent is hereby corrected as shown below:

On the title page item [73], after

"[73]  Assignee: Vical Incorporated, San Diego, Calif.", please insert -- and

[73]  Regents of the University of Michigan, University of Michigan, Ann Arbor, Mich. --.

Signed and Sealed this

Seventh Day of November, 2000

Attest:

Q. TODD DICKINSON

Attesting Officer

Director of Patents and Trademarks